(12) United States Patent
Fortuna et al.

(10) Patent No.: US 11,369,323 B2
(45) Date of Patent: Jun. 28, 2022

(54) RADIOLOGICAL IMAGING DEVICE WITH IMPROVED FUNCTIONALITY

(71) Applicant: Epica International, Inc., San Clemente, CA (US)

(72) Inventors: Damiano Fortuna, Florence (IT); Leonardo Manetti, Montevarchi (IT); Luca Ferretti, Pisa (IT); Denis De Micheli, Navacchio di Cascina (IT)

(73) Assignee: Epica International, Inc., San Clemente, CA (US)

( * ) Notice: Subject to any disclaimer, the term of this patent is extended or adjusted under 35 U.S.C. 154(b) by 6 days.

(21) Appl. No.: 16/882,743

(22) Filed: May 25, 2020

(65) Prior Publication Data

US 2020/0281545 A1    Sep. 10, 2020

Related U.S. Application Data

(63) Continuation of application No. 16/011,325, filed on Jun. 18, 2018, now Pat. No. 10,660,582, which is a
(Continued)

(51) Int. Cl.
*A61B 6/00* (2006.01)
*A61B 6/03* (2006.01)
*A61B 6/08* (2006.01)

(52) U.S. Cl.
CPC .............. *A61B 6/035* (2013.01); *A61B 6/032* (2013.01); *A61B 6/08* (2013.01); *A61B 6/4405* (2013.01);
(Continued)

(58) Field of Classification Search
CPC .. A61B 6/00; A61B 6/03; A61B 6/032; A61B 6/035; A61B 6/08; A61B 6/44;
(Continued)

(56) References Cited

U.S. PATENT DOCUMENTS 6,385,481 B2    5/2002    Nose et al.
6,751,283 B2    6/2004    van de Haar
(Continued)

FOREIGN PATENT DOCUMENTS

CN        1229627 A    9/1999
CN        1675656 A    9/2005
(Continued)

OTHER PUBLICATIONS

CN App. No. 201580009966.4 First Search Report, Feb. 24, 2020 (including translation from EPO Global Dossier).
(Continued)

*Primary Examiner* — Jurie Yun
(74) *Attorney, Agent, or Firm* — Steptoe & Johnson LLP; Robert Greenfeld

(57) ABSTRACT

A radiological imaging device includes a gantry defining an analysis zone in which at least a part of a patient is placed, a source that emits radiation that passes through the part of the patient, a detector that receives the radiation when performing at least one of tomography, fluoroscopy, radiography, and multimodality and generates data signals based on the radiation received, and a fluid-fed cooling system adapted to provide cooling for components that generate heat within the gantry.

12 Claims, 20 Drawing Sheets

Related U.S. Application Data continuation of application No. 14/932,806, filed on Nov. 4, 2015, now Pat. No. 10,016,171.

(60) Provisional application No. 62/078,800, filed on Nov. 12, 2014.

(52) U.S. Cl.
CPC .......... *A61B 6/4447* (2013.01); *A61B 6/4488* (2013.01); *A61B 6/508* (2013.01)

(58) Field of Classification Search
CPC ... A61B 6/4405; A61B 6/4488; A61B 6/4447; A61B 6/4452; A61B 6/508; G01N 23/00; G01N 23/046; G01N 23/08; G01N 23/083; H01J 35/12; H01J 35/105
See application file for complete search history.

(56) References Cited

U.S. PATENT DOCUMENTS

| | | | | |
|---|---|---|---|---|
| 7,001,045 | B2* | 2/2006 | Gregerson | A61B 6/035 362/253 |
| 7,194,061 | B2* | 3/2007 | Fujita | A61B 6/032 378/150 |
| 8,693,621 | B2* | 4/2014 | Thran | A61B 6/4447 378/17 |
| 9,880,292 | B2 | 1/2018 | Chiyoma et al. | |
| 10,016,171 | B2* | 7/2018 | Fortuna | A61B 6/4447 |
| 2013/0129104 | A1* | 5/2013 | Joshi | G10K 11/17857 381/71.3 |
| 2013/0343509 | A1* | 12/2013 | Gregerson | A61B 6/4476 378/4 |

FOREIGN PATENT DOCUMENTS

| | | |
|---|---|---|
| CN | 202785469 U | 3/2013 |
| CN | 103720485 A | 4/2014 |
| CN | 103814412 A | 5/2014 |
| EP | 0211086 A1 | 2/1987 |
| EP | 1393680 A1 | 3/2004 |

OTHER PUBLICATIONS

CN App. No. 201580009966.4 First Office Action, Feb. 27, 2020 (including translation from EPO Global Dossier).
CN App. No. 201580009966.4 Supplementary Search Report, Apr. 29, 2020 (translation from EPO Global Dossier).
CN App. No. 201580009966.4 Second Office Action, May 8, 2020 (including translation from EPO Global Dossier).

* cited by examiner

| Input Parameters | | | Output Configuration Parameters | | | |
|---|---|---|---|---|---|---|
| Imaging Procedure | Tissue Region of Interest | Patient Size | kV | mA | ms | Filter |
| Tomography | Hard / Head | Any | 100 | 30 | 10 | 3 mm Al + 0.2 mm Cu |
| Tomography | Hard / Thorax | Any | 100 | 60 | 5 | 3 mm Al + 0.2 mm Cu |
| Tomography | Soft / Abdomen | Any | 60 | 60 | 10 | 2 mm Al |
| Tomography | Soft / Limbs | Any | 60 | 30 | 15 | 2 mm Al |
| Radiography | Head | Small | 70 | 20 | 10 | 2 mm Al |
| Radiography | Thorax | Small | 80 | 25 | 2 | 2 mm Al |
| Radiography | Abdomen | Small | 75 | 30 | 10 | 2 mm Al |
| Radiography | Limbs | Small | 45 | 30 | 15 | 2 mm Al |
| Radiography | Head | Medium | 80 | 30 | 20 | 2 mm Al |
| Radiography | Thorax | Medium | 85 | 30 | 2 | 2 mm Al |
| Radiography | Abdomen | Medium | 80 | 40 | 10 | 2 mm Al |
| Radiography | Limbs | Medium | 50 | 30 | 20 | 2 mm Al |
| Radiography | Head | Large | 85 | 30 | 20 | 2 mm Al |
| Radiography | Thorax | Large | 95 | 30 | 2 | 2 mm Al |
| Radiography | Abdomen | Large | 90 | 60 | 20 | 2 mm Al |
| Radiography | Limbs | Large | 55 | 30 | 20 | 2 mm Al |
| Fluoroscopy | Head | Small | 70 | 20 | 5 | 2 mm Al |
| Fluoroscopy | Thorax | Small | 80 | 25 | 2 | 2 mm Al |
| Fluoroscopy | Abdomen | Small | 75 | 30 | 5 | 2 mm Al |
| Fluoroscopy | Limbs | Small | 45 | 30 | 5 | 2 mm Al |
| Fluoroscopy | Head | Medium | 80 | 30 | 5 | 2 mm Al |
| Fluoroscopy | Thorax | Medium | 85 | 30 | 2 | 2 mm Al |
| Fluoroscopy | Abdomen | Medium | 80 | 40 | 5 | 2 mm Al |
| Fluoroscopy | Limbs | Medium | 50 | 30 | 5 | 2 mm Al |
| Fluoroscopy | Head | Large | 85 | 30 | 5 | 2 mm Al |
| Fluoroscopy | Thorax | Large | 95 | 30 | 2 | 2 mm Al |
| Fluoroscopy | Abdomen | Large | 90 | 60 | 5 | 2 mm Al |
| Fluoroscopy | Limbs | Large | 55 | 30 | 5 | 2 mm Al |

*FIG. 2B*

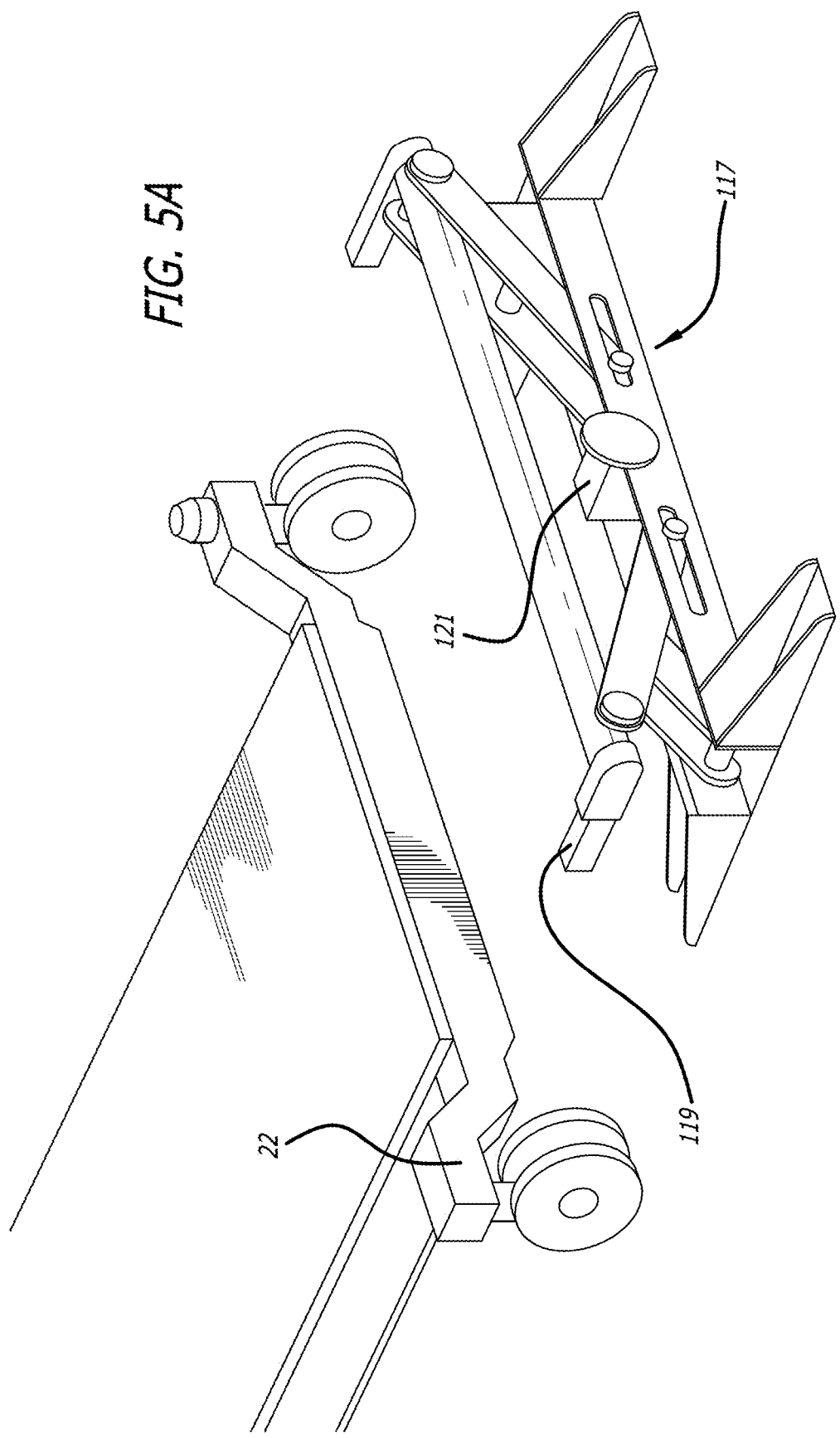

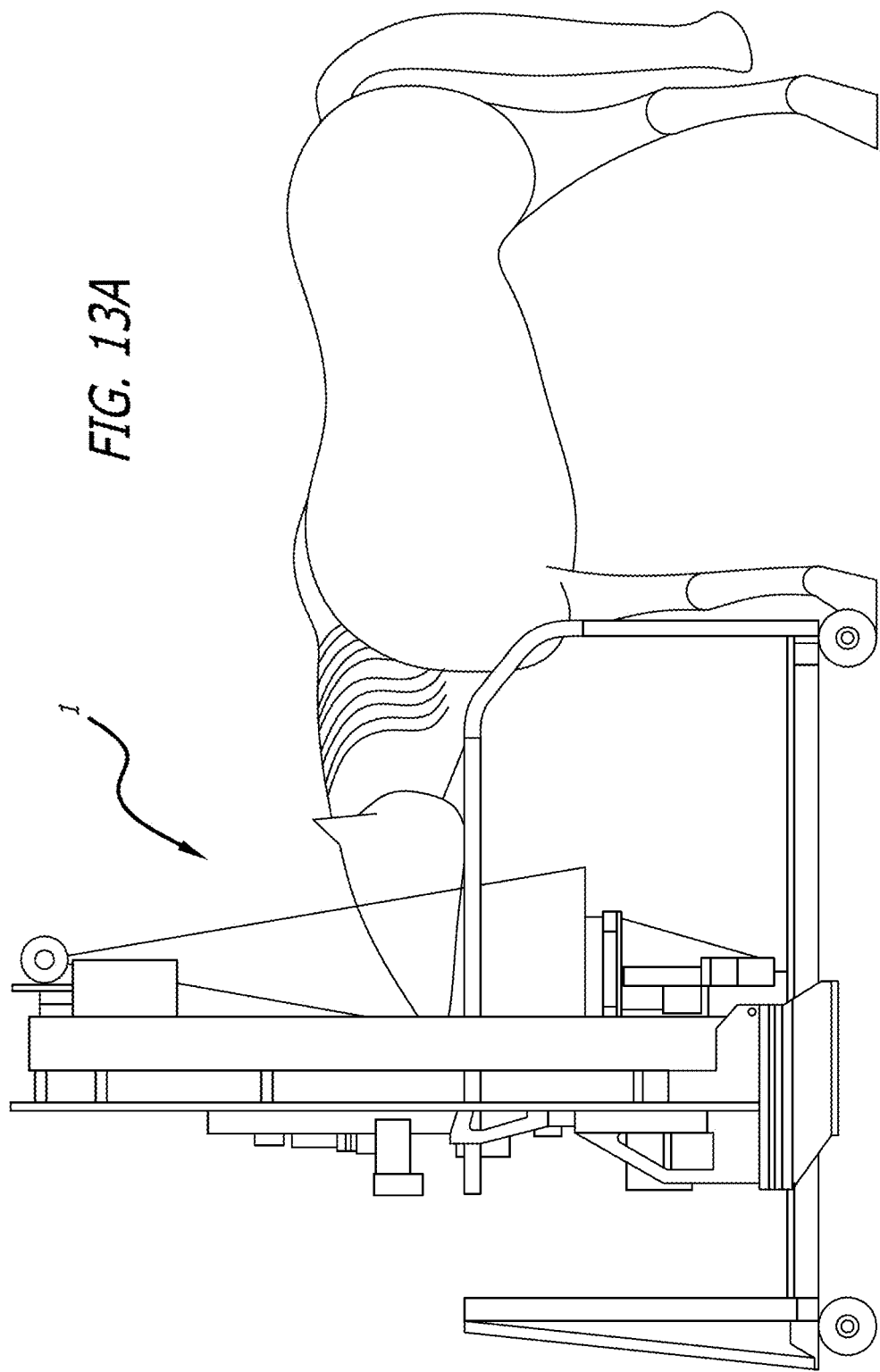

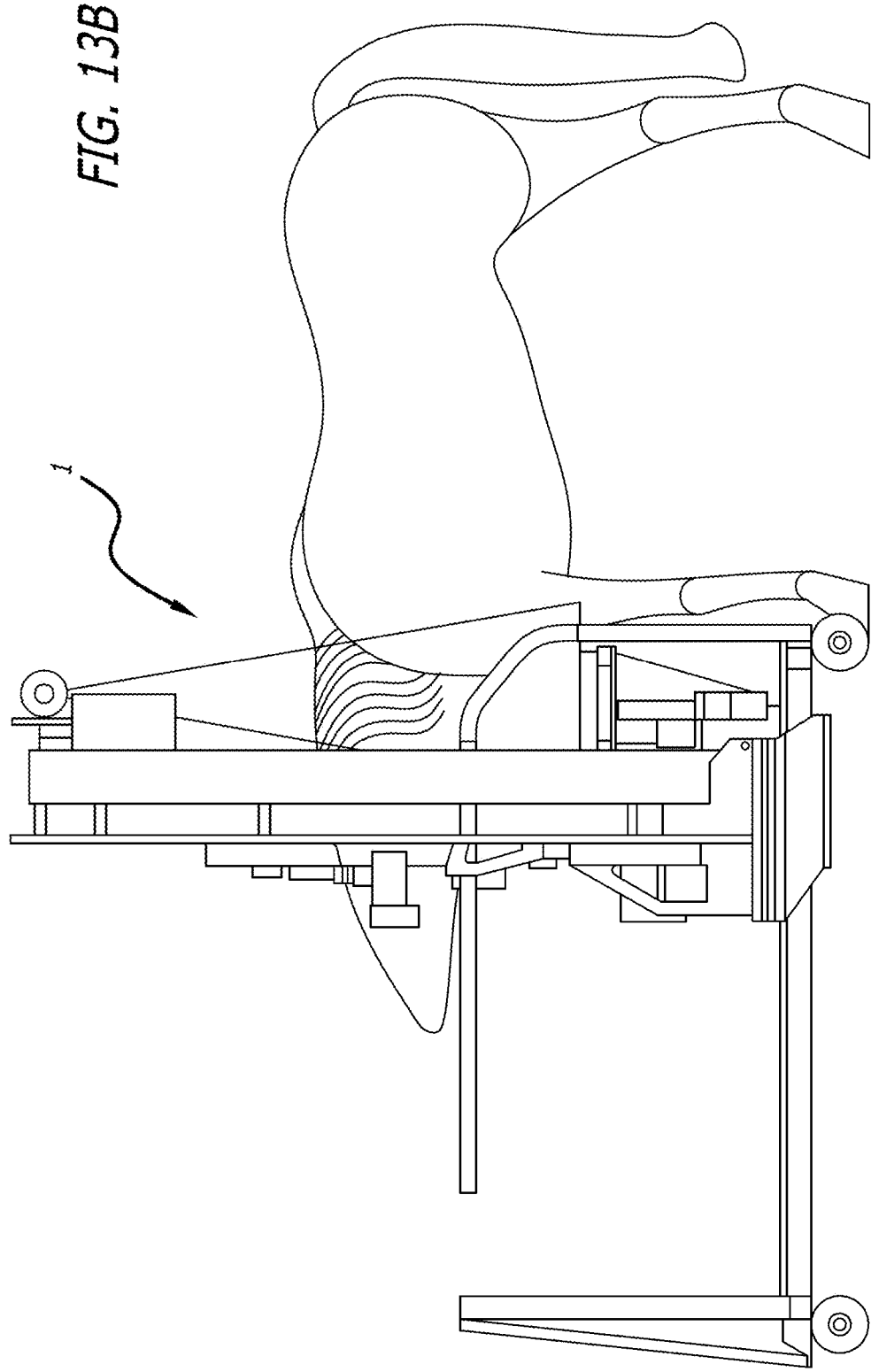

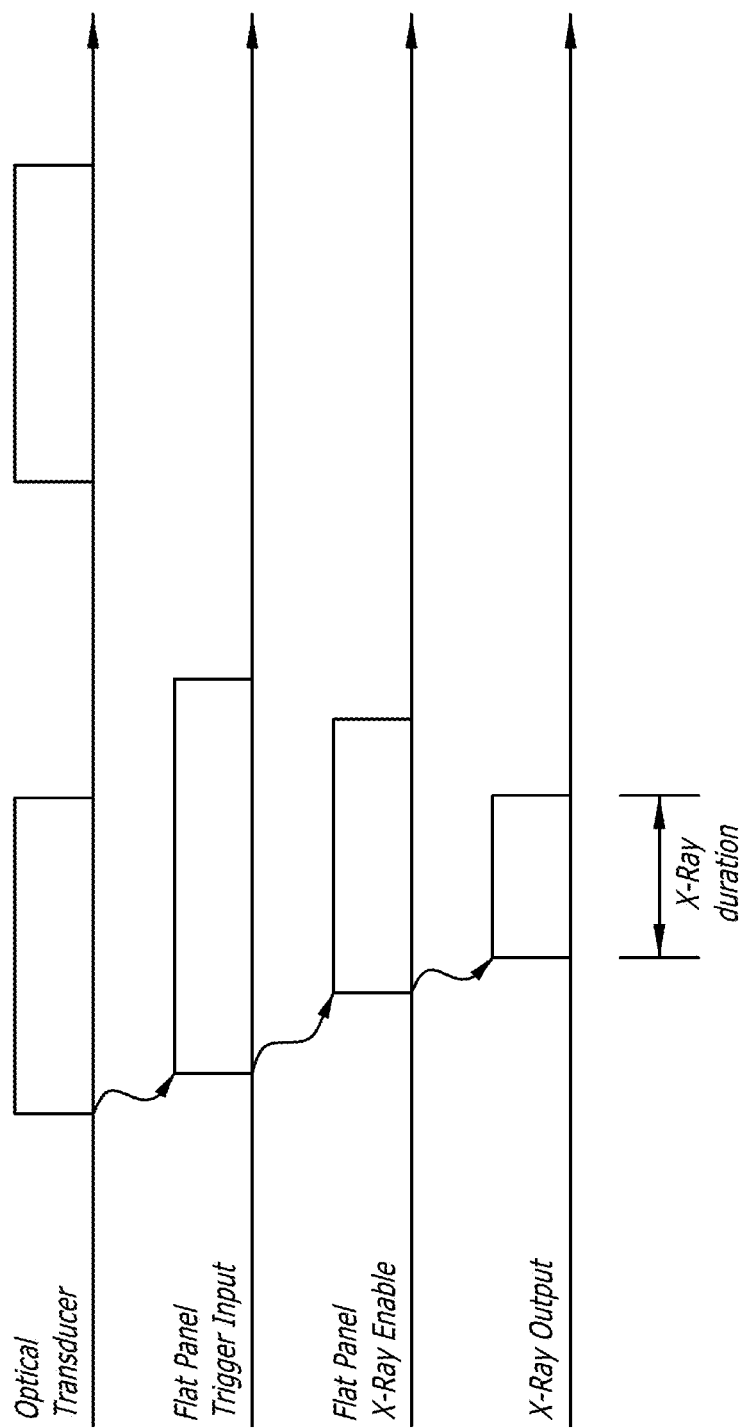

RADIOLOGICAL IMAGING DEVICE WITH IMPROVED FUNCTIONALITY

CROSS-REFERENCE TO RELATED APPLICATIONS

This application is a continuation of U.S. application Ser. No. 16/011,325, filed Jun. 18, 2018, now U.S. Pat. No. 10,660,582, which is a continuation of U.S. application Ser. No. 14/932,806, filed Nov. 4, 2015, now U.S. Pat. No. 10,016,171, which claims the benefit of U.S. Provisional Application No. 62/078,800, filed Nov. 12, 2014, the entire disclosures of which are hereby incorporated by reference. This application claims priority from U.S. Pat. Nos. 10,660,582 and 10,016,171 and U.S. Provisional Application No. 62/078,800.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The disclosure relates to obtaining radiological images, and, more particularly, to a device and method for performing a total body scan and reconstructing an image of a patient's entire body or an extensive portion thereof.

BACKGROUND

Many conventional imaging devices include a bed on which the patient is placed, a control station suitable to control the functioning of the device, and a gantry, that is, a device having a cavity in which the portion of the patient to be analyzed is inserted and suitable to perform the radiological imaging of the patient.

Inside the gantry, the radiological imaging devices are provided with a source suitable to emit radiation on command, such as X-rays, and a detector suitable to receive the radiation after it has traversed the portion of the patient to be analyzed and to send a signal suitable to permit visualization of the internal anatomy of the patient.

Typically, given the need to visualize extensive parts of the body, the detector used is a flat panel sensor, said flat panel sensor having a particularly extensive detection surface, which in some cases exceeds 1600 cm$^2$.

For example, flat panel sensors may be a direct-conversion type, and include a panel suitable to receive X-rays emitted by the source and to produce a series of electric charges in response, a segmented matrix of TFT in amorphous silicon which receives the aforementioned electric charges, and an electronic reading system. Flat panel sensors also may be an indirect-conversion type, including a layer suitable to receive X-rays emitted by the source and to produce a series of light photons in response (e.g., by scintillation), a segmented matrix of photodetectors (e.g., TFT, CMOS, CCD, and the like) that convert the aforementioned light photons into electric charges, and an electronic reading system. When radiation has struck the entire flat panel sensor, the electronic reading system determines the quantity of electric charge received by each TFT segment in a direct-conversion flat panel sensor or the quantity of electric charge generated by each photodetector of an indirect-conversion type of flat panel sensor, and correspondingly generates a matrix of numbers which represent the digital image.

However, flat panel sensors generally cannot absorb radiation continuously, owing to, for example, the particular interaction between the charges and the segmented matrix of TFT in amorphous silicon. Thus, in order to perform a total body scan of a patient's body, image acquisition of the patient's body is divided into a sequence of two-dimensional images, which are then reconstructed into a total body scan. In particular, reconstruction may require approximating the portions of the body located on edges between two successive images. Furthermore, other portions of the body may have to be reconstructed by approximation of a series of images of those portions. As a result, the use of flat panel sensors in this conventional manner results in poor quality radiological imaging, particularly in the case of total body scanning.

Moreover, the quality of conventional total body scans is also reduced as a result of diffused, so-called parasitic radiation, formed by the interactions between X-rays and matter, which hits the detector and thus degrades the quality of the image. In order to reduce the incidence of parasitic radiation, conventional radiological imaging devices are often fitted with anti-diffusion grids composed of thin lead plates fixedly arranged parallel to each other so as to prevent the diffused rays from reaching the flat panel sensor. However, such grids are only partially effective in remedying the effects of parasitic radiation on image quality. Furthermore, the use of anti-diffusion grids imposes the use of a higher dose, thereby possibly increasing the danger of causing illness.

Additionally, in order to perform different types of analyses to a high standard, a medical center must be equipped with several radiological imaging devices, involving substantial outlays. Moreover, conventional radiological imaging devices are characterized by high production costs and highly complex construction.

Accordingly, there has been a long felt need for a radiological imaging device for performing a total body scan and reconstructing a clear image of a patient's entire body or an extensive portion of a patient's body.

SUMMARY

Existing limitations associated with the foregoing, as well as other limitations, can be overcome by a method for operating a radiological imaging device, and by a system, apparatus, and computer program that operates in accordance with the method. Briefly, and in general terms, the present disclosure is directed to various embodiments of a radiological imaging device.

According to one embodiment herein, a radiological imaging device or system is disclosed. The radiological imaging device includes a gantry defining an analysis zone in which at least a part of a patient is placed; a source that emits radiation, that passes through at least part of a patient, where the radiation defines a central axis of propagation; and a receiving device that includes a detector that receives the radiation and is arranged on the opposite side of the patient with respect to the source. The detector detects radiation when performing at least one of tomography, fluoroscopy, radiography, and multimodality and generates data signals based on the radiation received.

The radiological imaging device also includes a horizontal gantry rotation apparatus that includes a ring to which the source and the detector are mounted, and a rotational bearing member configured to rotate the ring. The radiological imaging system further includes a control unit adapted to acquire an image from data signals received continuously from the detector while the horizontal gantry rotation apparatus continuously rotates the ring, the source emitting the radiation and the detector receiving the radiation that are mounted to the ring, so as to scan the at least part of the patient. In the radiological imaging system, the gantry is mounted to a transportation mechanism configured to transport the gantry.

In one example embodiment herein, the horizontal gantry rotation apparatus includes a low slip bearing member adapted to rapidly rotate the source and the receiving device in relation to an axis of a bore of the gantry (which may be the horizontal axis). The horizontal gantry rotation apparatus enables the rapid rotation of the source and the receiving device about the axis of the bore of the gantry in order to obtain a volumetric scan of the patient or at least a portion of the patient, with great stability and while minimizing slippage.

In another example embodiment herein, the radiological imaging device further includes a vertical gantry rotation apparatus configured to rotate the gantry about a vertical axis; a first lifter system and a second lifter system configured to lift each side of the radiological imaging device (front or back) simultaneously or independently; at least one positioning laser mounted on the gantry that projects a positioning guidance marker on the patient; and a cooling system connected to the source. The vertical gantry rotation apparatus includes a rotational base integrally attached to the gantry and adapted to rotate the gantry about an axis of rotation that is substantially perpendicular to the axis of the bore of the gantry. The vertical gantry rotation apparatus enables the rotation of the gantry about its vertical axis to thereby reduce the profile of the radiological imaging device and thus, provide ease in transportation of the device. The vertical gantry rotation apparatus also includes a first rotational plate mounted to the gantry and a second rotational plate mounted to the transportation mechanism.

In yet another example embodiment herein, a lifter system includes a scissor lift that slides underneath and connects to at least two sides of a transportation mechanism capable of supporting the gantry. The lifter system enables scanning of at least a part of a patient at varying angles of inclination (as well as providing a simple way to control elevation), which allows for decreased distances to scan targets and alignment of the gantry bore axis with target axes to increase image quality, improve the determination of the region of interest, and accommodate variable target heights and volumes. The lifter system further enables elevation of the gantry from one or both sides of the gantry and at varying heights and/or angles.

According to one example embodiment herein, a radiological imaging device further includes an integrated, roller support system that mounts to the gantry and is adapted to support a patient and/or a table, bed, or bed extension suitable to support the patient. In one example embodiment herein, the roller support system includes at least two vertical supports and at least one horizontal support mounted to the at least two vertical supports. In some embodiments, the at least one horizontal support includes at least one support roller. In some embodiments, the rolling support system includes a brace that is formed from a horizontal rolling bar reversibly mounted to at least two adjustable vertical bars, such that the at least two adjustable vertical bars are provided within a housing of the gantry.

In another example embodiment, the rolling support system can further include a fixed, cantilever support that includes at least two cantilever members attached to a brace that can be rotated to place the patient and/or the table, bed, or bed extension in the proper position. In any of the example embodiments, the rolling support system allows for the patient to be more easily placed into a desired position within the gantry, while avoiding interference with other components of the radiological imaging device.

According to another example embodiment herein, the radiological imaging device further includes a fluid-fed cooling system adapted to provide cooling for components that generate heat within the gantry. In one example embodiment herein, the cooling system includes a blow-through, fan-type cooling unit mounted to the source. The cooling system enables the performance of multiple scans in rapid succession by the radiological imaging device with minimal heat buildup.

According to yet another example embodiment herein, the radiological imaging device further includes a source tilting device that connects to the source and a translational apparatus configured to translate the detector. The source tilting device is adapted to position the source and thus, the central axis of propagation of the radiation at various angles depending on the scanning desired. In one example embodiment herein, the source tilting device includes a motor linked to an extendable piston system that engages with a source mounting plate and pivot to which the source is mounted. The source tilting device enables dynamic scanning that continually uses optimal offset distance and greater target volumes to be scanned by the gantry, increases the field-of-view (FOV) by altering the angle of radiation emitted by the source, and optimizes beam targeting by keeping the strongest beam of radiation focused on the receiving device. The source tilting device further reduces the need for a collimator utilizing a wide aperture, wide-angle emission, and multiple emission sources, which is beneficial given that these other components, if used, introduce greater technical difficulty, cost, power requirements, safety risks (due to emission), and inferior image quality.

In another example embodiment herein, the radiological imaging device also includes a translational apparatus arranged (i) to displace the at least one detector with respect to the source, and (ii) to displace the at least one detector horizontally with respect to interior edges of the gantry (i.e., side-to-side). In a further example embodiment herein, the translational apparatus includes a translational plate to which the at least one detector is mounted, a first linear actuator to move the at least one detector along a first direction of translation, and a second linear actuator to move the at least one detector along a second direction of translation. In yet another example embodiment herein, the first direction of translation is substantially perpendicular to the central axis of propagation and the second direction of translation is substantially parallel to the central axis of propagation. The translational apparatus allows for dynamic scanning, using elliptical and other rotational panel pathways, obtaining scans of at least a portion of the patient with improved image quality, increasing clearance of the gantry bore for scanning procedures, and increasing scanning diameter capabilities.

In one example embodiment herein, the at least one detector includes at least one flat panel sensor and/or at least one linear sensor. In an example embodiment in which the at least one detector is a flat panel sensor, the flat panel sensor is selectably operable in at least a flat panel mode and a linear sensor mode obtained, for example, by activating one or more pixel rows that are, preferably, substantially perpendicular to the axis of the bore. In a further example embodiment herein, in the flat panel mode, the sensor performs at least one of fluoroscopy and tomography, and, in the linear sensor mode, performs at least one of radiography and tomography.

In another example embodiment, the inclusion of the at least one horizontal gantry rotation apparatus, vertical gantry rotation apparatus, lifter system, rolling support system, cooling system, source tilting device, and translational apparatus, discussed above, in the radiological imaging device allows for the thickness of the gantry to be decreased. By decreasing the thickness of the gantry, the ease of access to the subject during positioning and image acquisition can be improved.

In further example embodiments, the at least one horizontal gantry rotation apparatus, vertical gantry rotation apparatus, lifter system, rolling support system, cooling system, source tilting device, and translational apparatus, discussed above, could also be included with the radiological imaging devices according to one or more of the example embodiments described in U.S. Provisional Patent Applications Nos. 61/932,024, 61/932,028, 61/932,034, and 61/944,956, which are incorporated herein by reference in their entireties, as if set forth fully herein.

In another embodiment, a method of acquiring a radiological image of at least a part of a patient placed in a gantry is disclosed. The method includes causing a source to emit radiation that passes through the at least a part of the patient, where the radiation defines a central axis of propagation. Also, the method includes receiving the radiation at a detector and outputting data signals from the detector to a control unit. The method further includes continuously rotating the source and the detector with a horizontal gantry rotation apparatus around a bore axis of the gantry, and acquiring, at the control unit, an image from data signals received continuously from the detector while the horizontal gantry rotation apparatus continuously rotates the source emitting the radiation and the detector receiving the radiation, so as to scan the at least part of the patient.

The method of acquiring a radiological image further includes mounting the gantry to a transportation mechanism configured to transport the gantry. The gantry is rotated about a vertical axis using a vertical gantry rotation apparatus. Further, the method includes lifting a first side of the transportation mechanism with a first lifter system and lifting a second side of the transportation mechanism with a second lifter system. The method may include projecting onto the patient at least one positioning guidance marker from at least one positioning laser mounted on the gantry.

According to further embodiments, the method of acquiring a radiological image includes adjusting the patient using a roller support system that mounts to the gantry. In this embodiment, the method includes cooling the source using a cooling system connected to the source. The method may include tilting the source using a source tilting device that connects to the source and translating a position of the detector in relation to the patient with a translational apparatus.

Other features will become apparent from the following detailed description taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2B illustrates a table containing predetermined relationships for configuring an X-ray source according to an example embodiment herein.

FIG. 5A illustrates a prospective view of a lifter system according to an example embodiment herein.

FIGS. 13A and 13B illustrate the radiological imaging device shown in FIG. 1 being used with an equine patient according to an example embodiment herein.

FIG. 14 illustrates a graph according to which the emission of X-rays by the radiation source and the acquisition of images via the radiation detector of the radiological imaging device are controlled.

DETAILED DESCRIPTION

Figure 1:
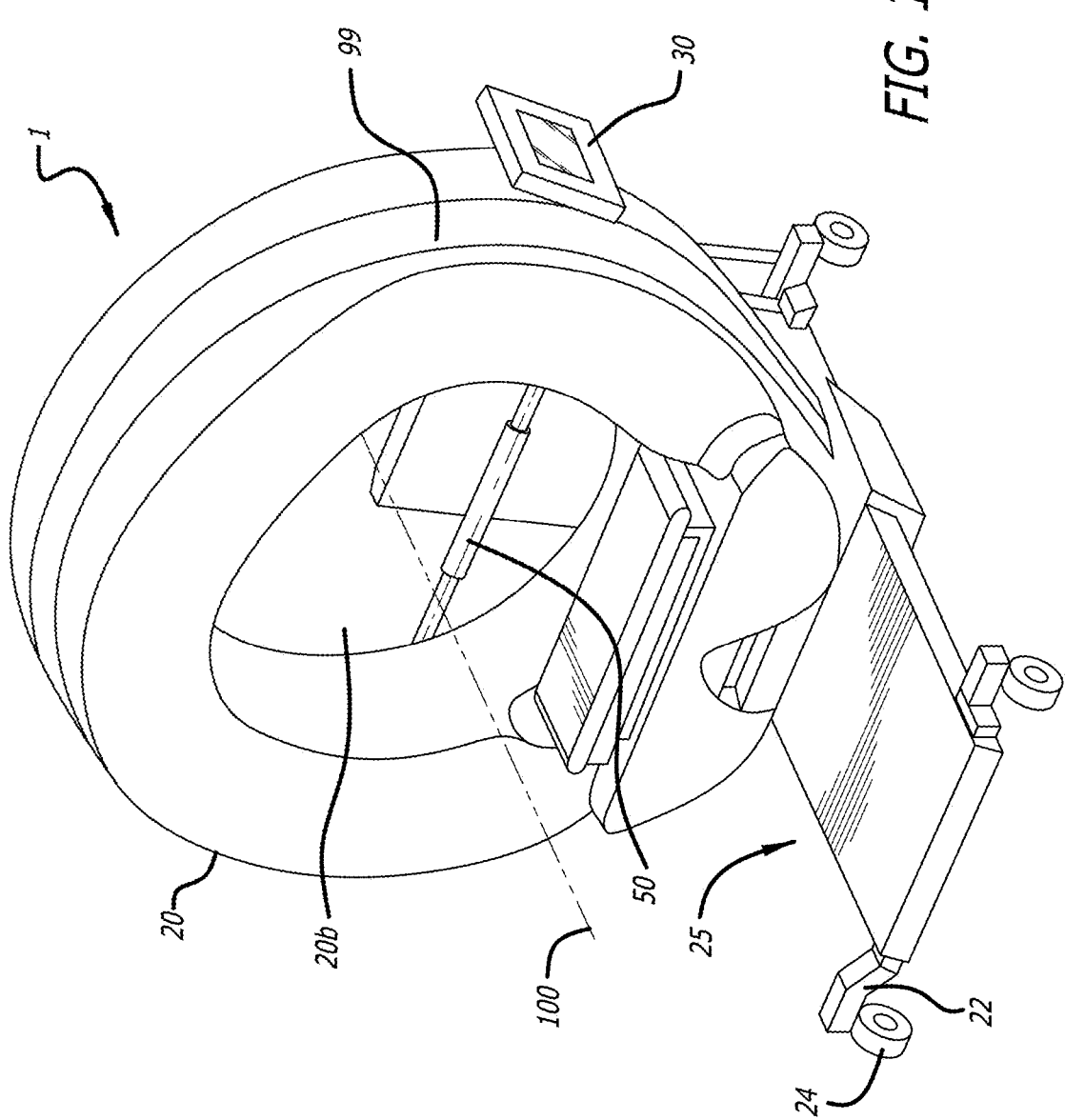
FIG. 1 illustrates a radiological imaging device according to an example embodiment herein.

Each of the features and teachings disclosed herein can be utilized separately or in conjunction with other features and teachings to provide a radiological imaging device or system with a bed. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of processes and symbolic representations of operations on data bits within a computer memory. These process descriptions and representations are the means used by those skilled in the data processing arts to most effectively convey the substance of their work to others skilled in the art. A process is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. The steps are not intended to be performed in a specific sequential manner unless specifically designated as such.

The methods or processes presented herein are not inherently related to any particular computer or other apparatus. Various general-purpose devices, computer servers, or personal computers may be used with programs in accordance with the teachings herein, or it may prove convenient to construct a more specialized apparatus to perform the method steps. The structure for a variety of these devices will appear from the description below. It will be appreciated that a variety of programming languages may be used to implement the teachings of the disclosure as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples.

With reference to FIGS. 1-14, reference numeral 1 denotes a radiological imaging device.

The different embodiments of the radiological imaging device 1, as disclosed herein, is useful in both the medical and veterinary applications for performing radiological imaging of at least one portion of the internal anatomy of a patient. In particular, the radiological imaging device 1 is useful for performing two and three-dimensional scans, and specifically, for selectively performing a radiography, a tomography (e.g., computerized tomography), a fluoroscopy, or a multimodality (see, for example, FIGS. 13A and 13B illustrating an example embodiment of the radiological imaging device 1 being used with an equine patient).

Referring to FIG. 1, there is shown a three dimensional perspective view of an embodiment of the radiological imaging device 1 configured for use in performing two and three dimensional scans on a patient's body. The radiological imaging device 1, includes a gantry 20 defining a preferred axis of extension 20a (indicated in FIG. 2c) and an analysis zone 20b in which at least part of the portion of the patient's body to be imaged is placed. The gantry also includes a transportation mechanism 25 and a control unit 30.

Figure 9A:
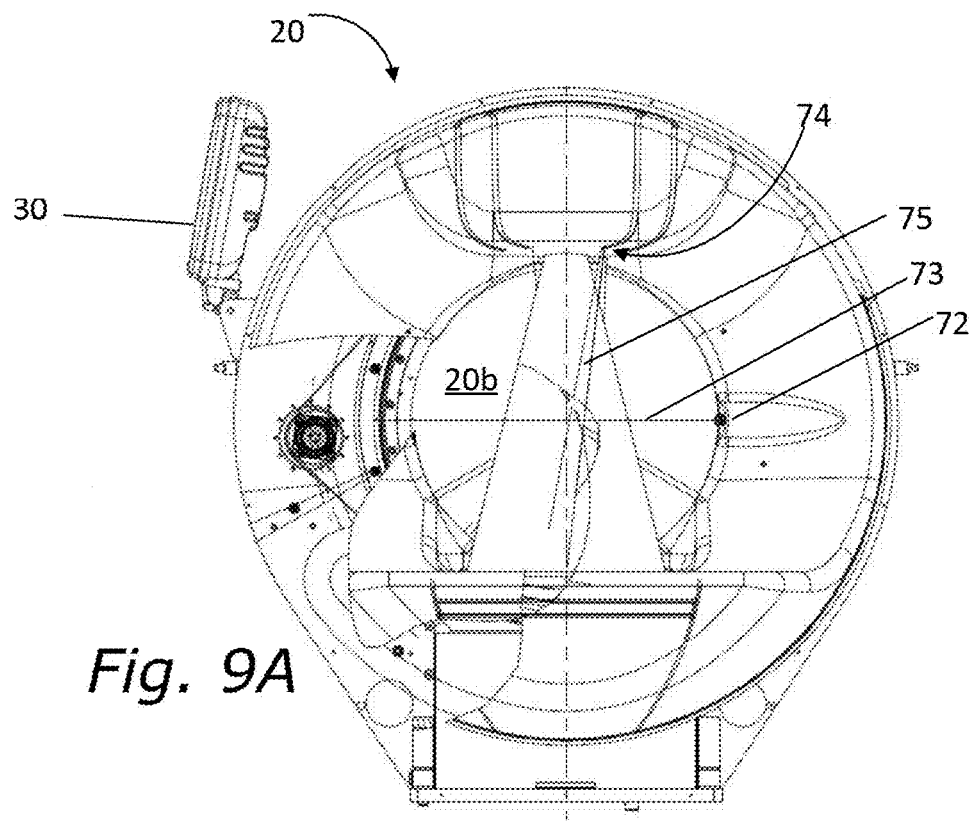
FIG. 9A illustrates a gantry subassembly with a cut-away portion, according to an example embodiment of the radiological imaging device of FIG. 1.
Figure 9B:
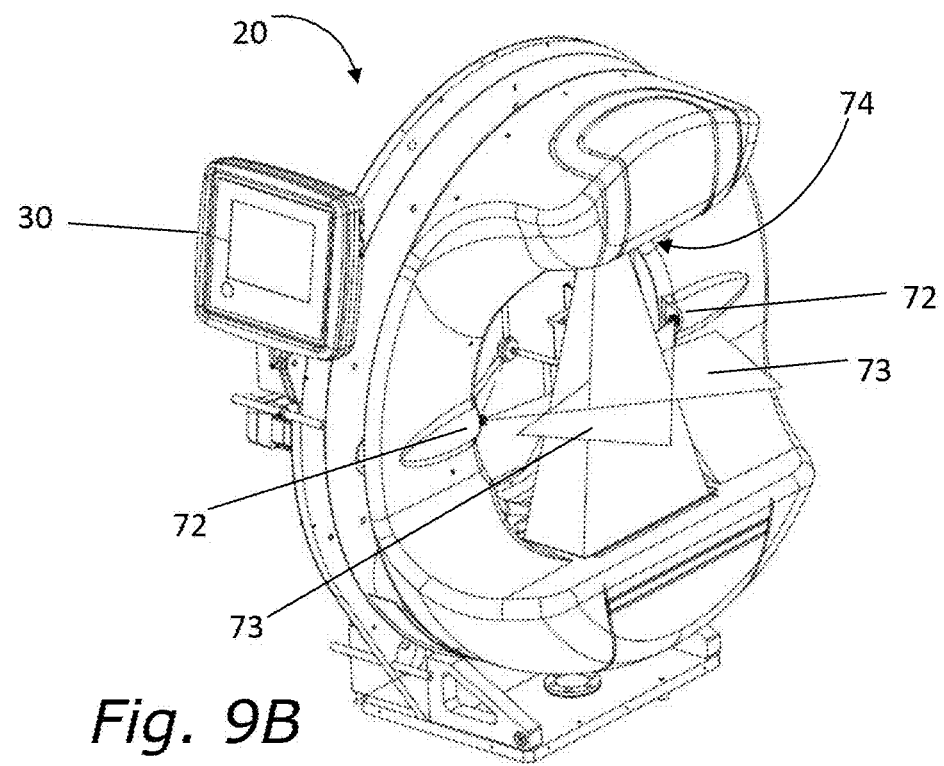
FIG. 9B illustrates a perspective view of the gantry subassembly shown in FIG. 9A.

The control unit 30 of the radiological imaging device 1 is mounted on the gantry 20 (as shown in FIGS. 1, 9A, and 9B) and is capable of controlling the gantry 20 by transferring data and command signal to gantry 20 using communication means. However, in some embodiments, the control unit 30 can be housed in a stand-alone unit (not shown) such as, for example, a workstation cart, or may be formed of multiple parts, such as, a first part mounted on the gantry 20 and a second part housed in a stand-alone unit. These examples are merely illustrative in nature, and in other embodiments, the control unit 30 can be located at other positions and locations besides those described above.

Figure 11:
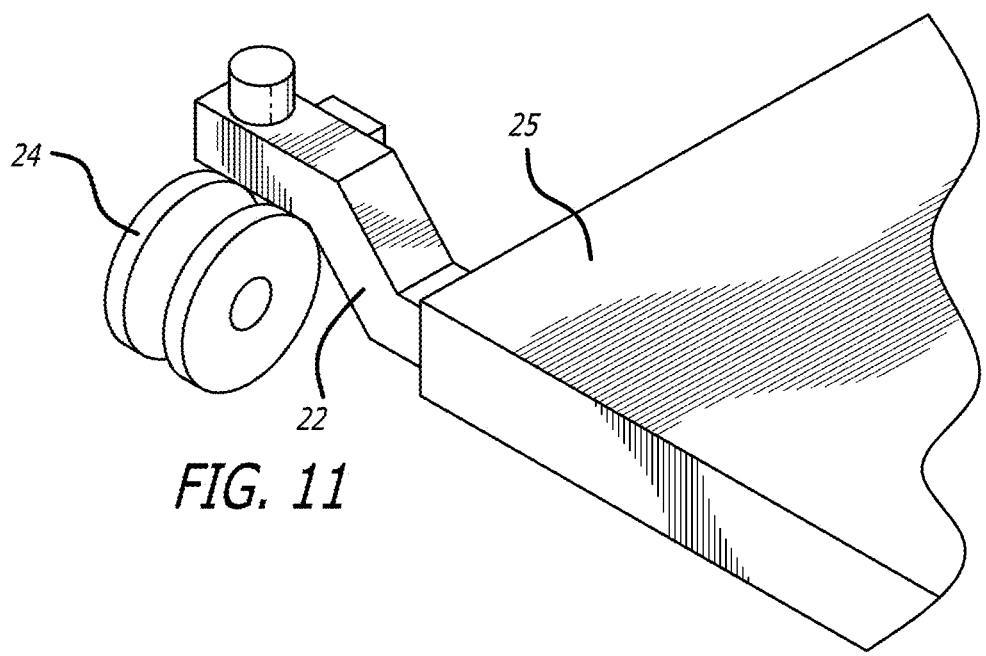
FIG. 11 illustrates a partial prospective view of an example embodiment of a transportation mechanism of the radiological imaging device shown in FIG. 1.

The gantry 20 is preferably mounted onto the transportation mechanism 25 (e.g., a cart) in order to be transported to a desired location. In one example embodiment, the transportation mechanism 25 includes at least four wheels 24 that are mounted to the transportation mechanism 25 via brackets 22. In one preferred embodiment, the brackets 22 are v-shaped (as shown in FIGS. 1 and 11) to accommodate wheels 24 of varying sizes, while still maintaining the transportation mechanism 25 as close to the floor as possible. Moreover, the v-shaped brackets allow the diameter of each of the wheels 24 to be substantially equal or preferably, substantially greater than the distance between the transportation mechanism 25 and the floor, which helps to maintain a constant distance between the transportation mechanism 25 and the floor. The distance between the transportation mechanism 25 and the floor is kept in a relatively small value, thus allowing the size of the gantry 20 to increase. However, a person skilled in the art would understand that any other suitable shape for the brackets 22 and/or any other means of attaching the wheels 24 to the transportation mechanism 25 can be used as well.

Figure 2A:
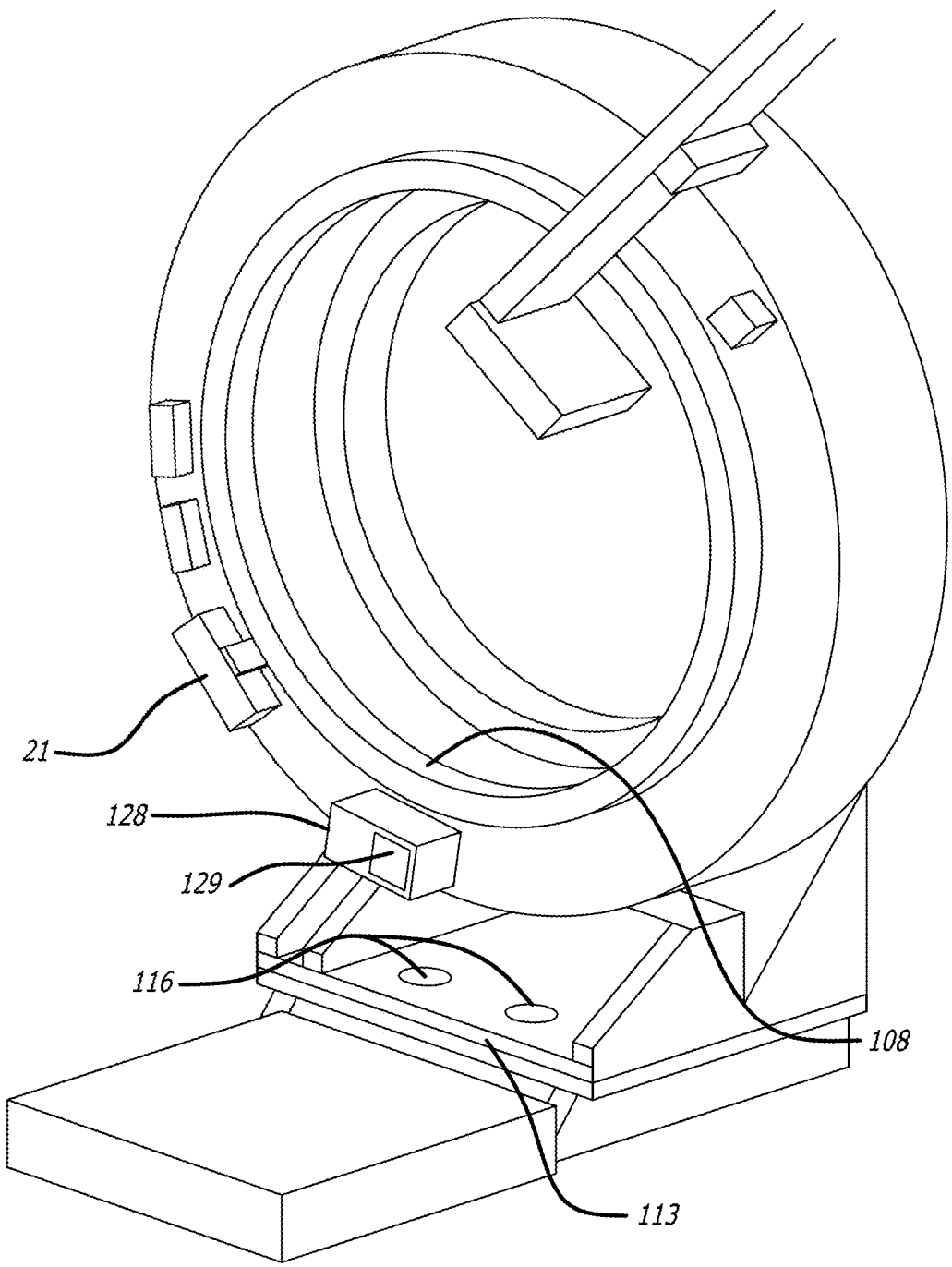
FIG. 2A illustrates a partial section showing internal structure of the radiological imaging device of FIG. 1.

In one embodiment, FIG. 2A shows a more detailed three dimensional perspective view of the gantry 20 and associated components of the radiological imaging device 1, as shown in FIG. 1. The gantry 20 in the radiological imaging device 1 includes a container 99 within which the various components used to perform the radiological scan are housed (see, for example, FIG. 1). The container 99 of the gantry 20 houses a radiation source 21 or the X-ray source (as in FIG. 2A) with a central axis of propagation 21*a* (shown in FIG. 2C), a radiation detector 102 or the Detector (as in FIG. 6C) to receive the radiation emitted by the radiation source 21. The gantry 20 further includes an analysis zone 20*b* in which the patient's entire body or a particular body part to be imaged is placed during scanning. In some embodiments, the gantry 20 also includes a laser positioning system that includes at least one horizontal laser 72 and one vertical laser 74 (FIGS. 9A and 9B).

The radiation source 21 or the X-ray source (as in FIG. 2A) emits radiation capable of traversing the patient's body and can interact with the tissues and fluids present inside the patient's body. In one embodiment, the radiation source 21 or the X-ray source (as in FIG. 2*a*) emits ionizing radiation, and more particularly, X-rays. Optionally, the radiological imaging device 1 includes a collimator adjacent to the radiation source 21 to focus the radiation on the radiation detector 102 or the Detector (as in FIG. 6C) and to modify the radiation field in order to adjust it to the position of the radiation detector 102 or the Detector (as in FIG. 6C).

Figure 2C:
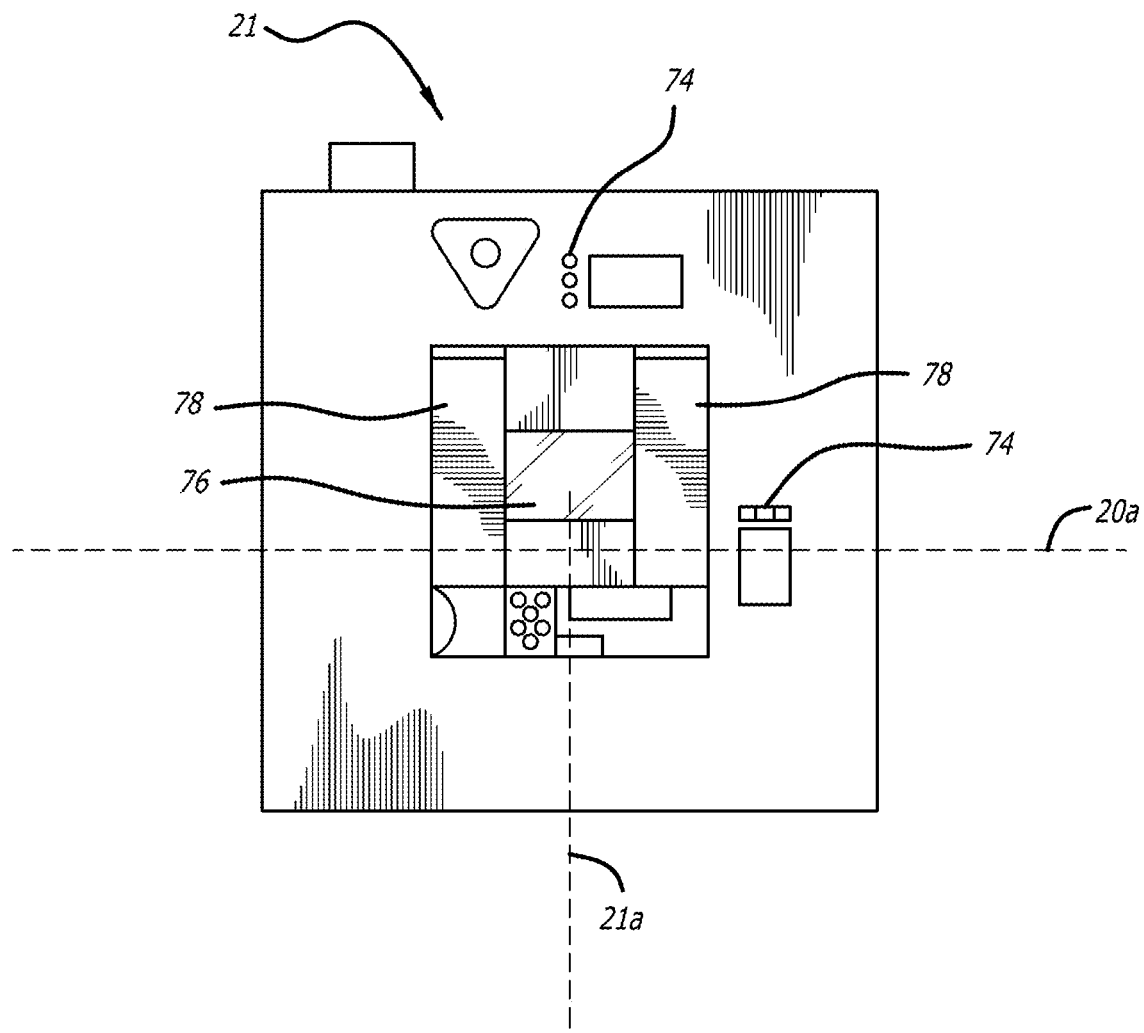
FIG. 2C illustrates a source subassembly of the radiological imaging device of FIG. 1 according to an example embodiment herein.

FIG. 2C shows a more detailed perspective view of the radiation source 21, as shown in FIG. 1 and its associated components. As mentioned above, the collimator 76 which is used to focus the radiation from the radiation detector 102 includes an X-ray filter 76*a* positioned between the radiation source 21 and the radiation detector 102. The X-ray filter 76*a* modifies the shape of the radiation beam (e.g. X-ray) emitted from the radiation source 21. The X-ray filter 76*a* also modifies the energy distribution of the emitted radiation along the axis of propagation 21*a* by absorbing the low power X-rays prior to the X-rays traversing the patient. In one embodiment, the X-ray filter 76*a* includes a sheet material (e.g., aluminum and/or copper sheet) of predetermined thickness suitable for absorbing the radiation. The thickness of the radiation absorbing sheet is calculated along the axis of propagation 21*a*.

In another example embodiment herein, a plurality of X-ray filters 76*a* (not shown) are stored at different locations in the gantry 20. Each X-ray filter 76*a* of the multiple X-ray filters differs from other at least in terms of material (such as an aluminum and/or copper sheet) of the sheet or thickness of the sheet. The control unit 30 can cause a motorized mechanism (not shown) provided within the gantry 20 to retrieve a selected X-ray filter (e.g., selected by control unit 30 in a manner to be described further herein below) from storage and position the selected X-ray filter in front of the source 21.

In a further example embodiment herein, the operator inputs patient specific information, for example, the types of imaging procedures (e.g., fluoroscopy, tomography, or radiography) to be performed on the patient, the species of the patient (e.g., human or animal), the patient's weight, tissue type to be imaged or the like, in the control unit 30. Based on the inputted information, the control unit 30 automatically configures an optimal radiation dosage to be used on the patient by the radiological imaging device 1. Moreover, based on some predetermined relationships among the different patient specific information, the control unit 30 determines the emission energy of the X-rays and/or the type of X-ray filter 76*a* to be placed in front of the radiation source 21. Examples of such predetermined relationships are shown in the table of FIG. 2B, which are defined in accordance with look-up tables, conditional statement algorithms, and/or mathematical formulas implemented on the control unit 30. Accordingly, the radiological imaging device 1 can perform the selected imaging procedure with an X-ray dosage that is safe for the patient, as well as the operator, while maintaining optimal image quality. The emission energy of the X-rays depends on parameters, such as, X-ray tube voltage, X-ray tube current, and exposure time.

For example, the control unit 30 can perform the aforementioned determination of X-ray emission energy and/or select an X-ray filter type based on predetermined relationships (e.g., defined in accordance with look-up table(s), conditional statement algorithm(s), and/or mathematical formula(s) implemented on control unit 30, although these examples are not limiting) between the patient information, the radiological imaging procedure selected to be performed, the X-ray emission energy, and the materials and thicknesses of the X-ray filters available in the plurality of X-ray filters located inside the gantry. Examples of such predetermined relationships are shown in the table of FIG. 2*b*. By way of example and not of limitation, if while inputting the patient specific information in the control unit 30, an operator specifies that a high resolution tomography is to be performed on hard tissues (e.g., a thorax region), the control unit 30 can determine the operating parameters of the radiation source 21 for such specification using a look up table (for example, FIG. 2C). Specifically, using the lookup table of FIG. 2C, the control unit 30 can determine that the aforementioned input correlates to operating parameters for the radiation source 21 of 100 kV and 60 mA for 5 ms, and for the X-ray filter 76*a* with a 3 mm thick aluminum sheet and a 0.2 mm thick copper sheet (FIG. 2B). As another example, if an operator specifies (by way of the control unit 30) that high resolution tomography is to be performed on soft tissues (e.g., an abdominal region), the control unit 30 determines, via the look-up table of FIG. 2C, that that the aforementioned input correlates to operating parameters for the radiation source 21 of 60 kV and 60 mA for 10 ms and an X-ray filter 76*a* with a 2 mm thick sheet of aluminum (see FIG. 2B). Such variables can be adjusted depending on the target being scanned.

In yet another embodiment, the radiation source 21 emits either a cone-shaped beam or a fan-shaped beam of radiation using the collimator 76, which can modify the beam shape. The collimator 76, as shown in FIG. 2C, includes at least two movable plates 78, preferably, four movable plates, surrounding the area of X-ray emission and therefore, substantially blocking the radiation. An operator can place the movable plates 78 of the collimator 76 in an open configuration, a slit configuration or in between those configurations using a motorized mechanism (not shown) controlled by the control unit 30. The operator can also configure the movable plates 78 along an axis of translation which is substantially perpendicular to the axis of propagation 21*a* and substantially perpendicular or parallel to the axis of extension 20*a*, using the motorized mechanism controlled by the control unit 30.

In some embodiments, the motorized mechanism includes at least one independent motor for each movable plate 78 and an additional motor for the X-ray filter 76*a*. When the collimator 76 is configured in the open configuration, radiation from the radiation source 21 is not blocked and travels along the axis of propagation 21*a* in the shape of a cone. However, when the collimator 76 is configured as a slit, a portion of the radiation of the radiation source 21 is blocked, and thus the unblocked radiation propagates along the axis of propagation 21*a* in the shape of a fan (i.e., a cross-section of the cone-shaped radiation) oriented in a plane perpendicular to the direction of extension 20a. Thus, in one example embodiment herein, an operator may configure the source 21 to emit either a cone-shaped beam or a fan-shaped beam by virtue of the collimator 76, and perform different types of imaging with the radiological imaging device 1, for example, cone beam tomography or fan beam tomography, respectively.

In another embodiment, the shape of the beam of radiation emitted by the radiation source 21 can be modified by positioning a filtering means (not shown) on top of the radiation source 21 to focus the beam of radiation onto the target. In particular, in one embodiment, the radiation source 21 can emit radiation in a plurality of fan-shaped beams of radiation by using the filtering means. By using a plurality of fan-shaped beams, the image quality of the scanned image can be improved due to, inter alia, reduction of light scattering as compared to cone-shaped radiation emission. In yet another embodiment, the filtering means includes, for example, one or more filters, one or more grids or an adjustable diaphragm. In addition, in another embodiment, the filtering means can include one more stackable filters or stackable grids. In some embodiments, the filtering means is movable.

In one embodiment, the laser positioning system, which includes horizontal laser 72 and vertical laser 74, is used in conjunction with an adjustable bed. The laser positioning system, when activated on the control unit 30, projects visual markers onto the patient in order to facilitate positioning of the patient on a bed within the analysis zone 20b. Further details can be found in U.S. Provisional Patent Applications No. 61/932,034 and 61/944,956, which are incorporated herein by reference in their entireties.

Referring again to the drawings and more particularly to FIGS. 9A and 9B, there is shown one embodiment of the gantry 20 of the radiological imaging device 1 of FIG. 1. As mentioned above the laser positioning system is mounted on the gantry 20 and includes at least one horizontal laser 72 and/or at least one vertical laser 74. The horizontal laser 72 projects horizontal visual markers 73 to aid the operator in adjusting the height and inclination of the patient and the vertical laser 74 projects a top-down marker 75 to aid the operator in adjusting the lateral centering of the patient with respect to the gantry 20. The operator adjusts the positioning of the patient by observing the position of the patient with respect to the projected laser markers 73 and 75, and thus with respect to the analysis zone 20b. The operator then manually repositions the patient on the bed by adjusting controls of the bed (not shown in FIGS. 9A and 9B) until the patient is in the correct position for imaging. In one embodiment, two mutually oblique horizontal lasers 72 are provided in order to reciprocally intersect and define a horizontal marker segment. In the example embodiment, the two horizontal lasers 72 project visual markers at opposite angles to each other along an inclined axis.

In some embodiments, in the analysis zone 20b the radiation detector 102 is located opposite to the radiation source 21 and collimator 76 to detect radiation once it has traversed the portion of the patient's body to be examined. Once the radiation is received, the radiation detector 102 convers the received radiation into equivalent electrical signal and transfers the signal to the control unit 30 at a particular frame rate. Once received, the control unit 30 processes the data signals to acquire images. One exemplary method of controlling the emission of radiation by the source and the detection of the radiation by the receiving device will be described more fully below.

In one embodiment, the gantry 20 includes a horizontal gantry rotation apparatus 40 (FIGS. 3A-3C) to rotate the radiation source 21 and the radiation detector 102 together around the axis of extension 20a to allow the radiological imaging device 1 to perform a 360° scanning of the portion of the patient that has been placed in the analysis zone 20b (FIG. 1). In another embodiment, the horizontal gantry rotation apparatus 40 rotates the radiation (X-ray) source 21 and the radiation detector 102 rapidly around the axis of the bore of the gantry 100 (FIG. 1) in order to obtain a volumetric scan of a patient. The rapid rotation of the source and the receiving device about the bore axis of the gantry 100 (namely, the axis of extension 20a) using the horizontal gantry rotation apparatus 40, can be accomplished with great stability while minimizing the slippage.

Figure 3A:
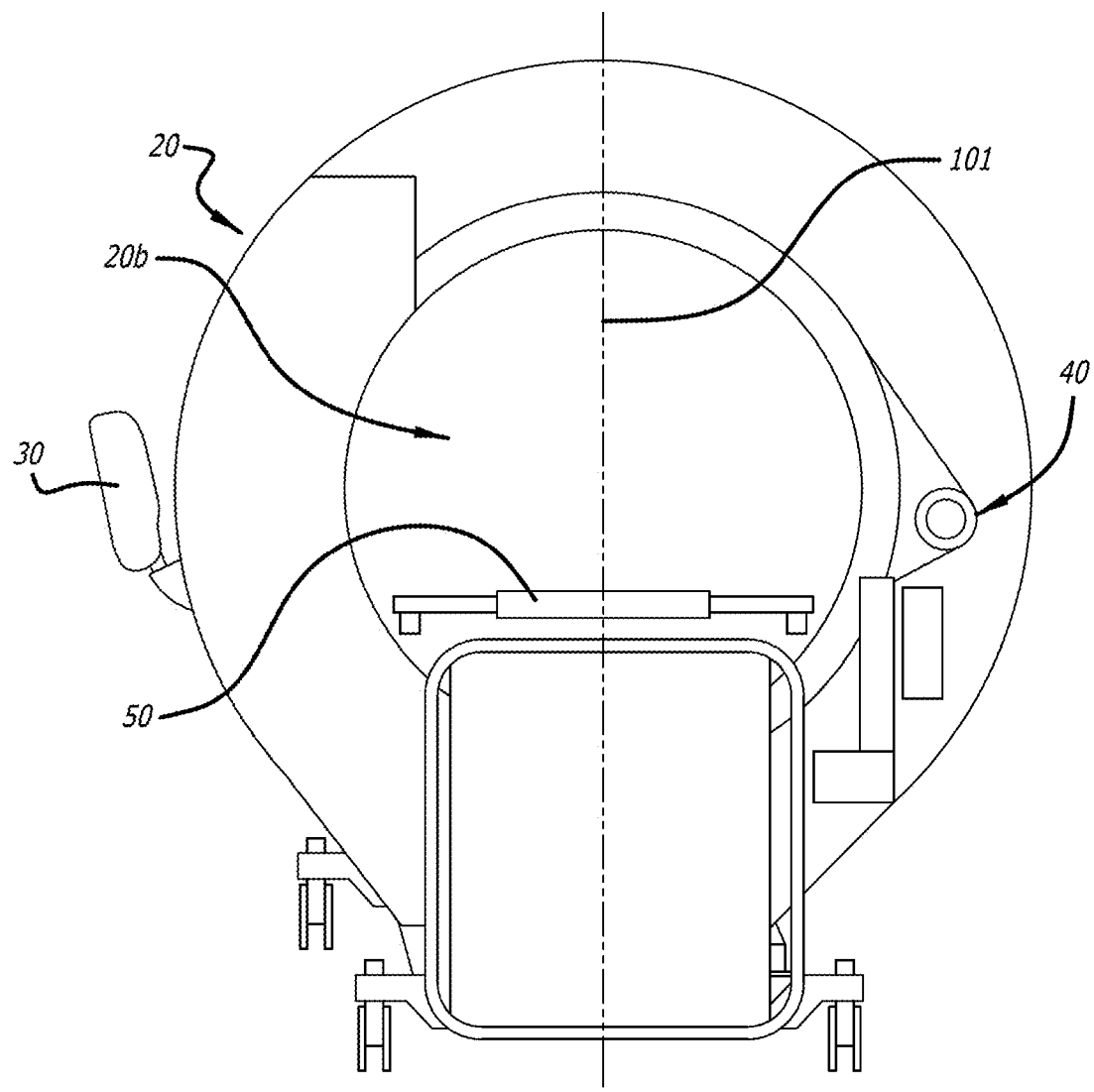
FIG. 3A illustrates another view, partly in cross-section of the radiological imaging device of FIG. 1.
Figure 3B:
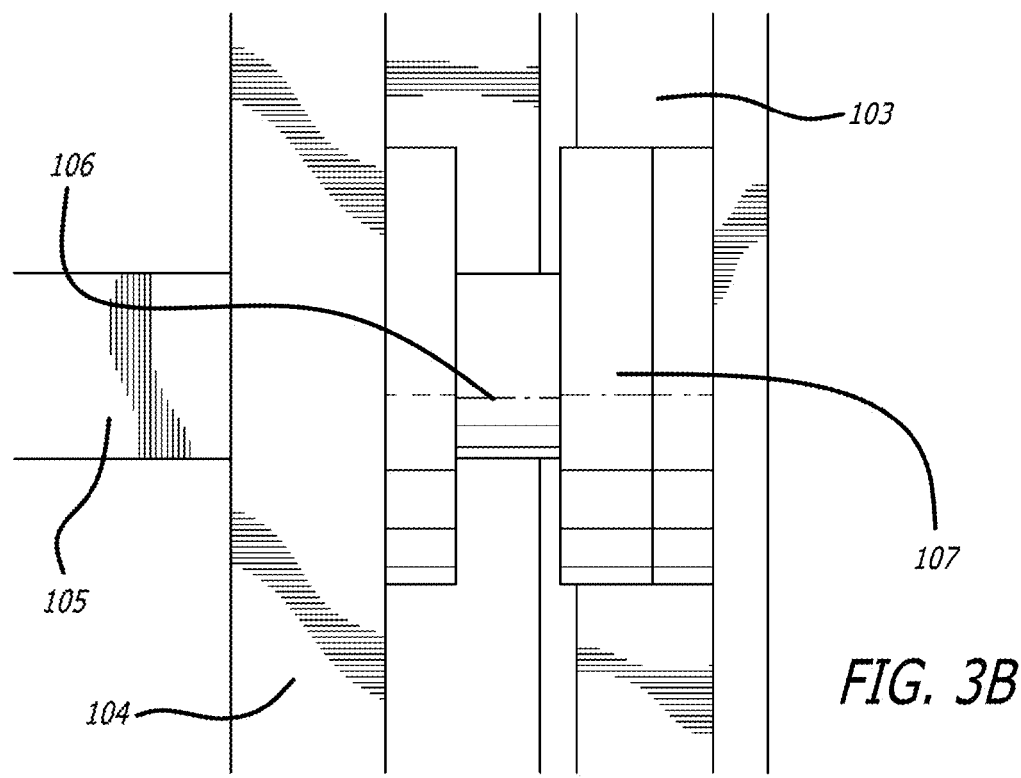
FIG. 3B illustrates a partial view of an example embodiment of the horizontal gantry rotation apparatus of the radiological imaging device of FIG. 3A.
Figure 3C:
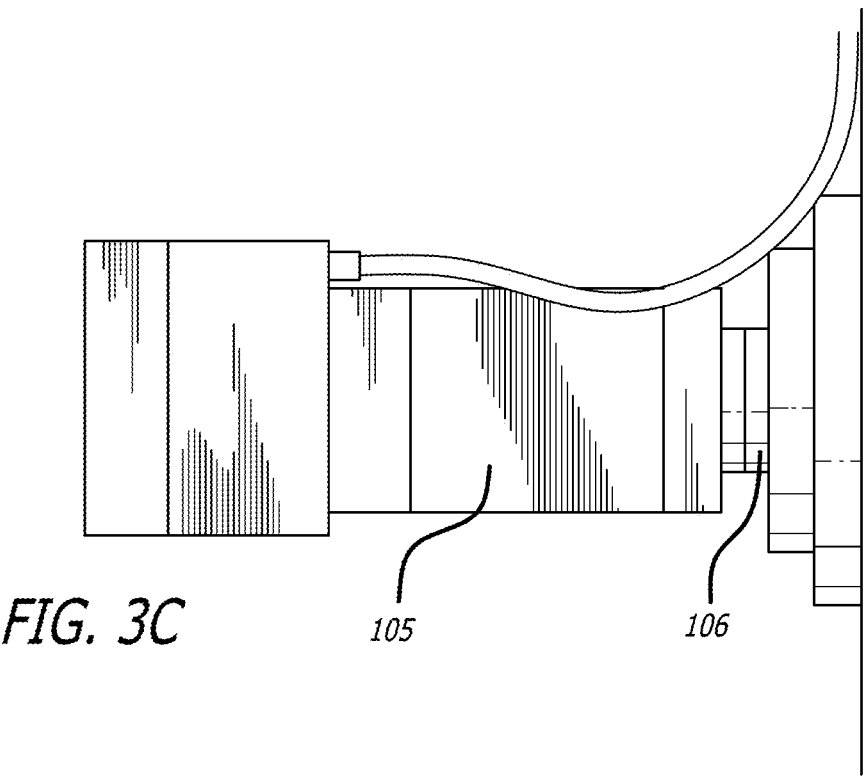
FIG. 3C illustrates another partial view of the example embodiment of the horizontal rotation apparatus of the radiological imaging device of FIG. 3B.
Figure 4A:
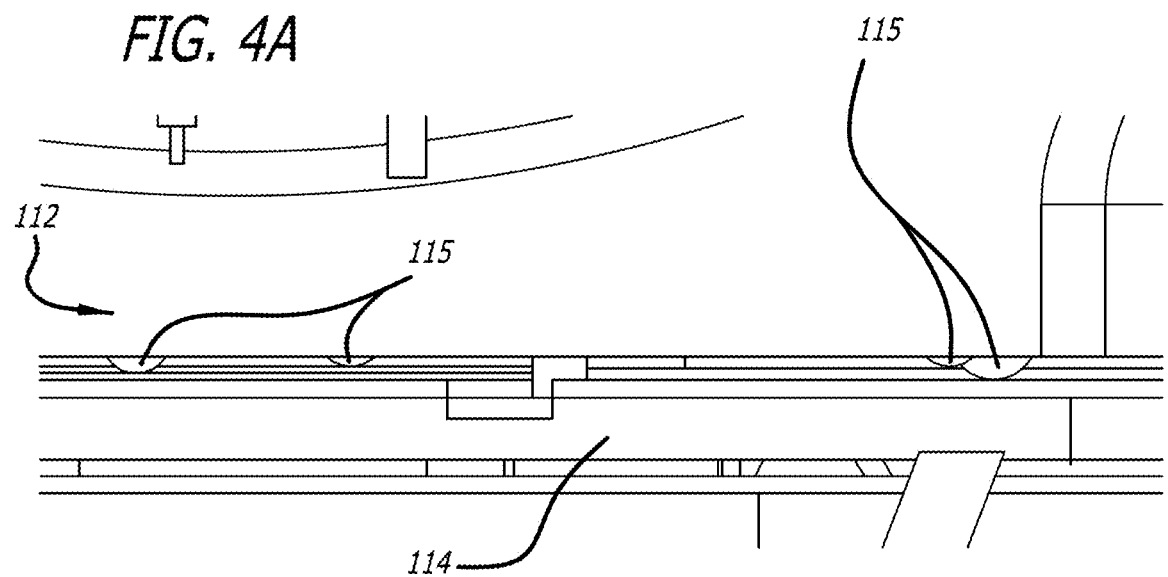
FIG. 4A illustrates a partial view of an example embodiment of the vertical gantry rotation apparatus of the radiological imaging device of FIG. 2A.
Figure 4B:
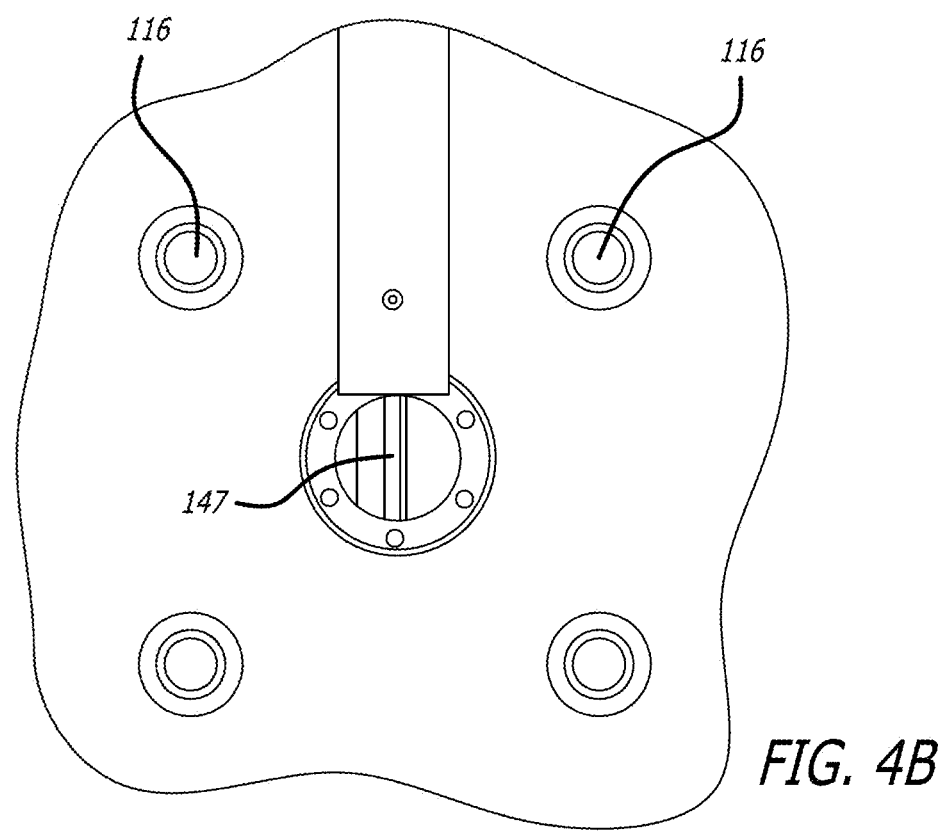
FIG. 4B illustrates further detail, partly in section, of the example embodiment of the vertical gantry rotation apparatus of FIG. 4A.
Figure 5B:
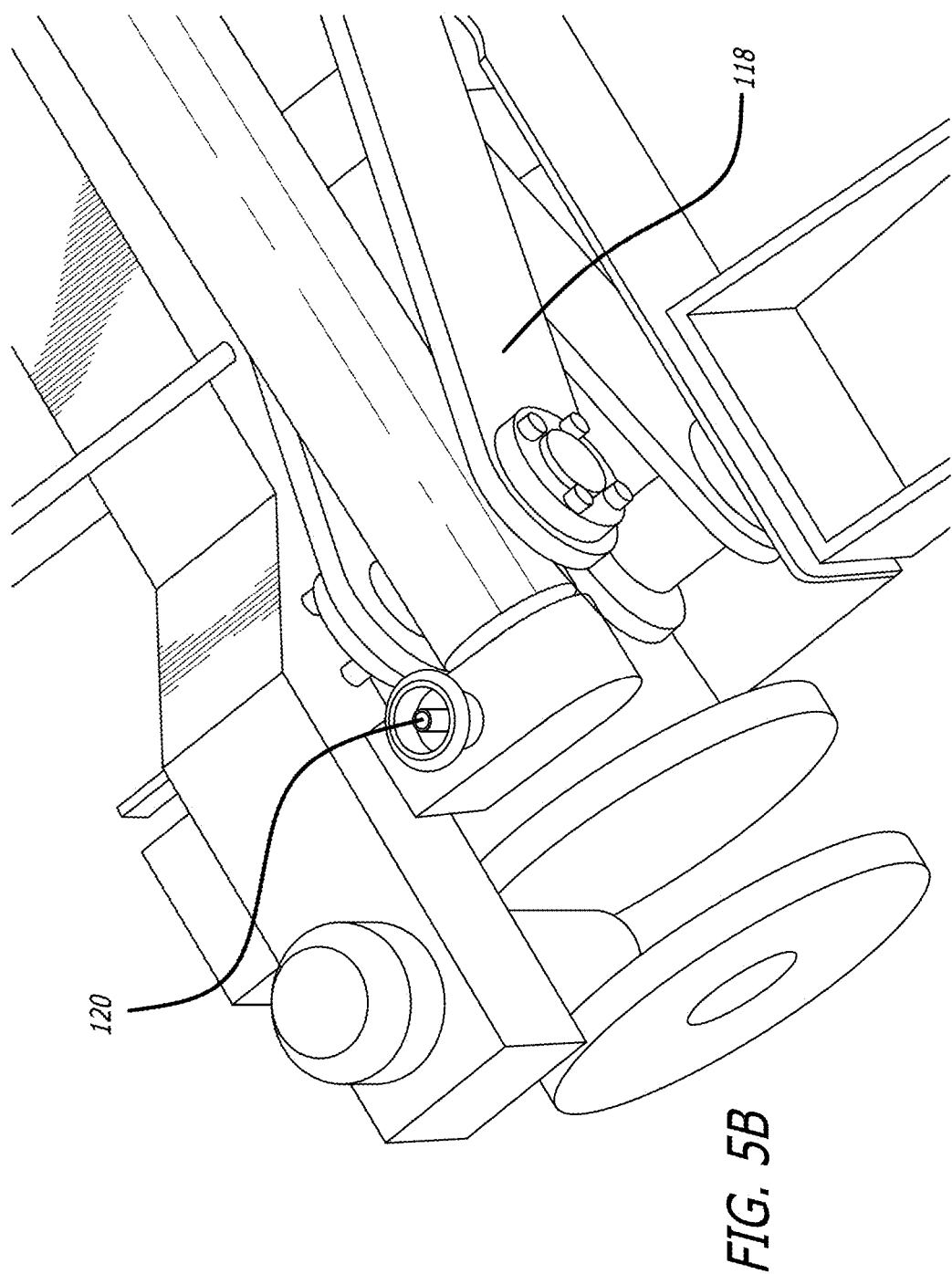
FIG. 5B illustrates a partial top view of the example embodiment of the lifter system of FIG. 5A.
Figure 5C:
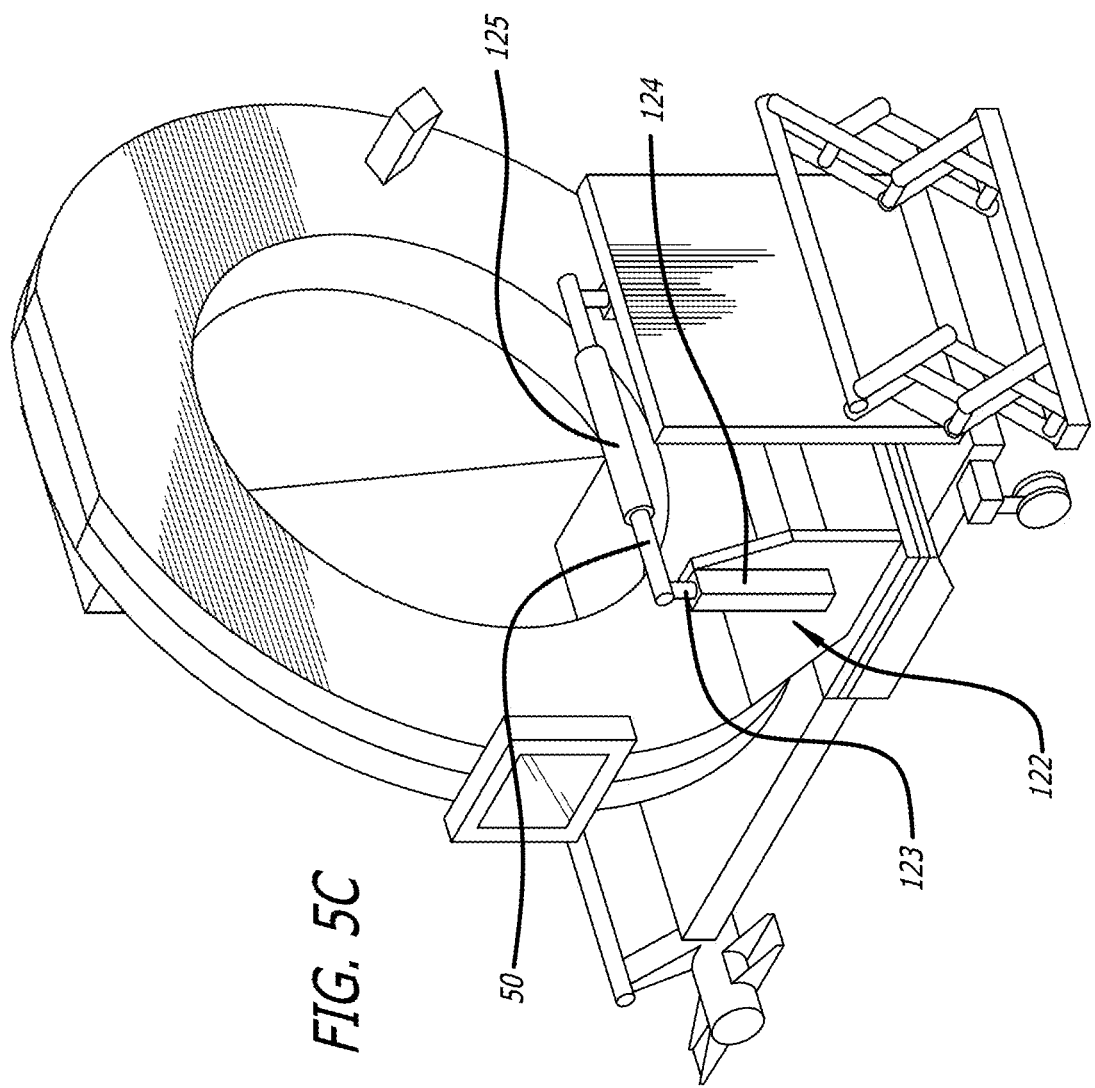
FIG. 5C illustrates a sectional view of the radiological imaging device of FIG. 1 including the rolling support system and the lifter system according to an example embodiment herein.
Figure 6A:
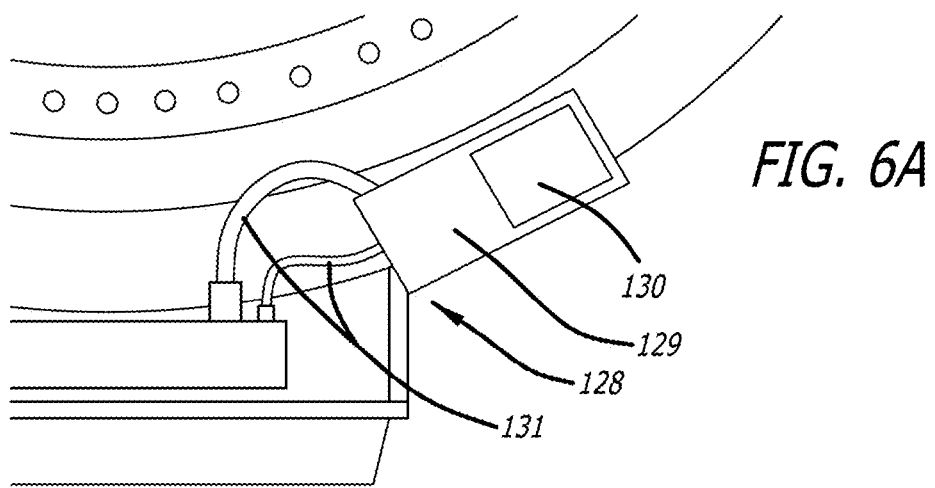
FIG. 6A illustrates a configuration of the cooling system according to an example embodiment herein.
Figure 6B:
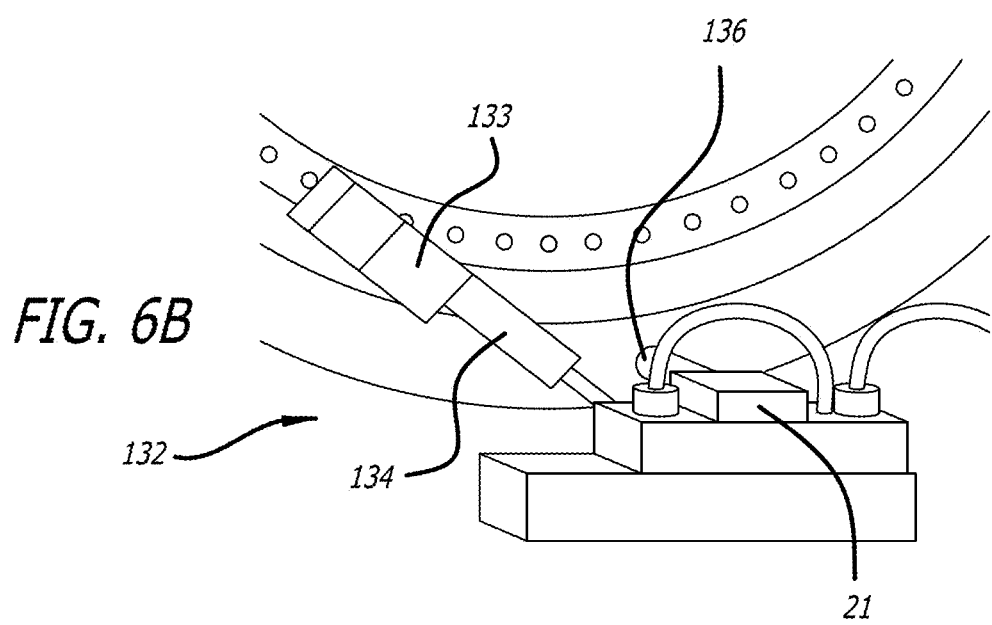
FIG. 6B illustrates a configuration of the source tilting device according to an example embodiment herein.
Figure 6C:
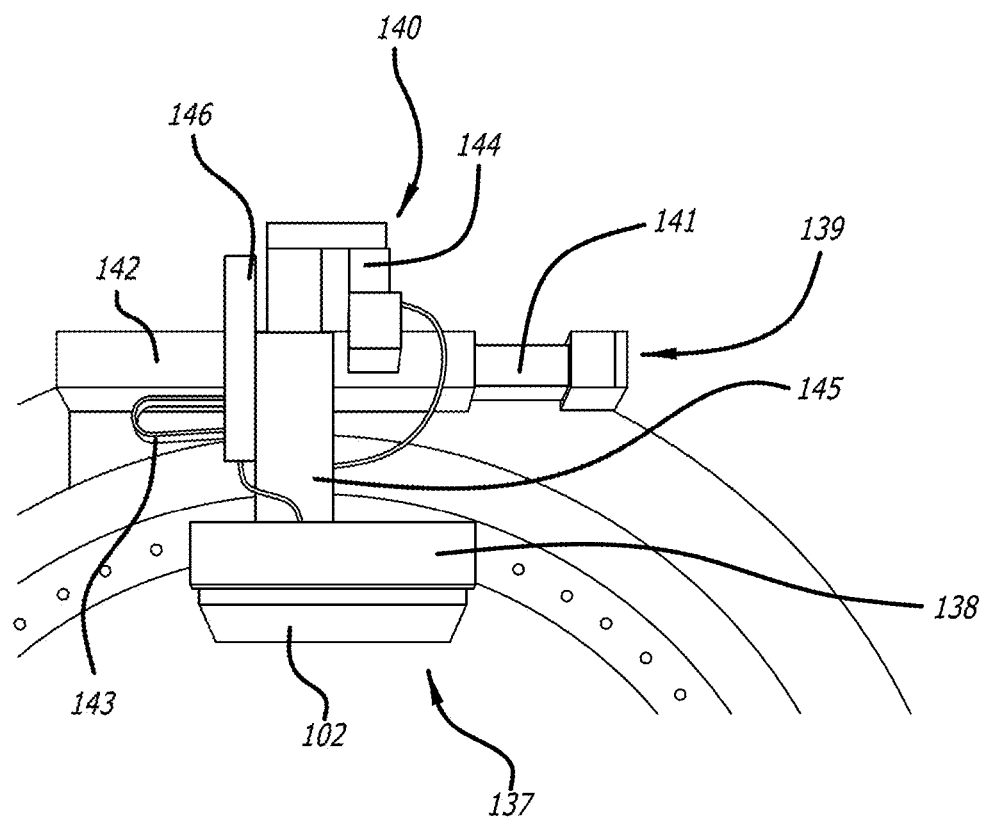
FIG. 6C illustrates the translational apparatus of the radiological imaging device of FIG. 1 according to an example embodiment herein.

In some embodiments, the horizontal gantry rotation apparatus 40 includes a gantry source/detector ring 103 or gantry source/detector ring of FIG. 3B to which the radiation source 21 and the radiation detector 102 are mounted, and a static ring 104 connecting the gantry source/detector 103 ring to the transportation mechanism 25. In one embodiment, the gantry source/detector ring 103 can be attached to the static ring 104 in a cantilever manner.

The horizontal gantry rotation apparatus 40 further includes a rotational motor 105 or horizontal gantry axis rotation motor (FIGS. 3B-3C) that is integral with the static ring 104, a gearbox 106 or horizontal gantry axis rotation gearbox that is driven by the motor 105, and a rotational bearing 107 or horizontal gantry axis rotation bearing of FIG. 3B interposed between the rings. The rotational bearing 107 includes a low-slip bearing member and is connected to the gearbox 106. The rotational bearing 107 which is housed inside of the gantry 20, drives the rotation of the gantry source/detector ring 103 via a rotational contact of the rotational bearing 107 to the gantry source/detector ring 103. In particular, the motor 105 drives the gearbox 106, which in turn rotates the rotational bearing 107, which thus, rotates, with respect to the static ring 104, the gantry source/detector ring 103 through the contact between these two members. Operation of the motor 105 and thus, the rotational bearing 107 can be controlled by the control unit 30. In some embodiments, it is preferred to minimize slippage between the rotational bearing 107 and the gantry source/detector ring 103, such that these two members rotate substantially in unison, and the loss of control over the rotation is minimized. In some other embodiments, the amount of friction between the rotational bearing 107 and the gantry source/detector ring 103 is desired to be increased in order to minimize the slippage between these members. The amount of friction can be increased by, for example, producing these members out of materials having desired coefficients of friction or by adding various coatings or texturing to one or both of these members to achieve a desired coefficient of friction.

In one embodiment, the gantry 20 further includes a perforated, laser-tracked ring 108 or the laser tracking ring (FIG. 2A) integrated with the gantry source/detector ring 103 that records data relating to rotation of the gantry source/detector ring 103 about the bore axis 100 of the gantry 20. A laser emitter 109 and a detector 110 (not shown) that detects openings (e.g., perforations uniformly and angularly spaced by 0.5 degrees) in the perforated, laser-tracked ring 108 as the ring rotates around the bore axis 100, are used to record data relating to the gantry 20 rotation. By recording the data relating to the gantry 20 rotation, both the orientation and the speed of the gantry source/detector ring 103 can be monitored and analyzed using various software embedded in the control unit 30, which in turn can reduce slippage and potential errors in the gantry 20 rotation. In another embodiment, by detecting the openings in the perforated, laser-tracked ring 108, the slippage between the rotational bearing 107 and the gantry source/detector ring 103 can be minimized.

In some embodiments, the motion of the gantry source/detector ring 103 is controlled by a standard closed-loop method. In this closed loop method, as the gantry source/detector ring 103 rotates, the laser emitter 109/detector 110 provides pulses as the openings in the perforated, laser-tracked ring 108 are detected. In order to determine whether an error in the positioning of the gantry source/detector ring 103 has occurred due to, for example, motion slippage, the desired motion of rotation of the gantry source/detector ring 103 is defined as an angle $\theta$.

Following is a method of minimizing slippage between the rotational bearing 107 and the gantry source/detector ring 103 of the gantry 20, as described in FIG. 1. The method starts with applying accelerating rotation on the gantry source/detector ring 103 by until the gantry source/detector ring 103 in a desired velocity (with any suitable velocity shape). As the gantry source/detector ring 103 is accelerated up to the desired velocity, pulses are counted in order to compute the real or actual angular span or displacement ($\alpha$), which occurs during the accelerated motion. Once the gantry source/detector ring 103 reaches a constant velocity of rotation, the pulses are continuously counted in order to track the real angular position (given by the angle $\beta$) of the gantry source/detector ring 103. The real angular position of the gantry source/detector ring 103 can be calculated from the following formula:

$$\beta=\theta-\alpha+\Delta,$$

where, $\Delta$ corresponds to a relatively small angle equivalent to a few pulses. Once, the gantry source/detector ring 103 reaches the angular position of $\beta$ it is subjected to a deceleration to bring it to a stop following the velocity curve used in the acceleration phase in reverse, so that the angular span during this deceleration phase is substantially equal to $\alpha$. In this disclosed embodiment, it is preferred that the final angular position of the gantry source/detector ring 103 is substantially equal to $\theta+\Delta$ A during rotation, since the role of $\Delta$ is to assure that the final number of pulses is at least equal to the desired number of pulses, given that an extra pulse is acceptable.

In another exemplary method of minimizing slippage between the rotational bearing 107 and the gantry source/detector ring 103, the values of $\alpha$, $\beta$, $\theta$ and $\Delta$ are defined in the same manner. However, in this embodiment, a standard velocity loop is used. Moreover, in this embodiment, a velocity shape is defined (e.g., trapezoidal or S-shaped) for the point-to-point motion of the gantry source/detector ring 103 from zero (0) to $\theta$, and a relationship between the angle $\beta$ and the desired angular velocity is computed. For each detected pulse, a counter is incremented, allowing for the tracking of angle $\beta$. Once the counter reaches the desired angular velocity, i.e., $\beta=\theta-\alpha+\Delta$, such that the last desired pulse is detected, the rotation of the gantry source/detector ring 103 is definitively stopped. Thus, in this exemplary embodiment, the extra stroke $\Delta$ is not needed to implement the method.

The detecting of the openings (i.e., perforations) in the perforated, laser-tracked ring 108 can also be used to drive the emission of the radiation via the radiation source 21. In particular, in one embodiment, the detecting of each opening in the perforated, laser-tracked ring 108 via the laser emitter 109/detector 110 combination as the ring rotates around the bore axis 100 can be used to drive the emission of the radiation via the radiation source 21. Alternatively, detecting every other opening, or every third opening, or every fourth opening, etc., in the perforated, laser-tracked ring 108 via the laser emitter 109/detector 110 combination can be used to drive the emission of the radiation via the radiation source 21.

According to another embodiment, the emission of X-rays by the radiation source 21 and the acquisition of images via the radiation detector 102 of the radiological imaging device 1 are controlled according to the graph of FIG. 14. In this embodiment, an optical transducer 111, provided on a fixed position of the gantry 20, gives an accurate signal (as shown in FIG. 14) for each mechanical position of the gantry source/detector ring 103 with respect to the required resolution. The accurate signal provided by the optical transducer 111 is generated as each opening, or every other opening, or every third opening, etc. in the perforated, laser-tracked ring 108 is detected via the optical transducer 111. The number of openings detected in the perforated, laser-tracked ring 108 is dependent upon the desired resolution of the scanned images (e.g., 720 pulses/revolution). The signal from the optical transducer 111 is used to generate a trigger signal or Flat Panel Trigger Input, as shown in FIG. 14, to drive the radiation detector 102 (e.g.; the flat panel sensor) acquisition. Accordingly, the radiation detector 102 generates a dedicated signal or the X-Ray Enable (in FIG. 14) to indicate that the panel is ready to be irradiated by the X-ray source.

Continuing with the embodiment with respect to FIG. 14, when the signal generated by the radiation detector 102 or the X-Ray Enable (in FIG. 14) goes high, the internal electronics circuitry of the radiological imaging device 1 drives the X-Ray source or the X-Ray Output in FIG. 14, to produce an irradiation of the desired duration. In the event that the signal from the radiation detector 102 or the X-Ray Enable (in FIG. 14) goes low, the radiation detector 102 (e.g.; the flat panel sensor) should no longer be irradiated. Irradiation of the detector when this signal is low (e.g., disabled) lead to artifacts in the acquired images, which in turn can lead to poor image quality. Accordingly, in this embodiment, the internal electronics circuitry of the radiological imaging device 1 prevents it from producing poor quality images. Although, the embodiment described above utilizes a single optical transducer 111, multiple optical transducers can be provided in order to optimize the scanning of images by the radiological imaging device 1. Furthermore, in yet another embodiment, the radiation detector 102 shall no longer be irradiated when the output signal gets high or low and, therefore, changes, in order to have up to 1440 pulses/revolution.

The specific components and configuration of the horizontal gantry rotation apparatus 40 of the embodiment of the radiological imaging device 1, as discussed above can be altered without departing from the spirit of the invention. In another embodiment, for example, the horizontal gantry rotation apparatus 40 can include at least one of horizontal or vertical wheels in a guide track, a base with a wheel seat for the gantry, treads, gears, an electric rotational motor, air-separated, magnetically-balanced or lubricated contacting rings, direct-drive motors, or manual manipulation. Moreover, a volumetric scan of the patient or at least a portion of the patient can alternatively be obtained, for example, by way of a scanning tube (e.g., CT scanning tube) or by using C-arm or robotic arm sensors and source mounts.

In some embodiments, a vertical gantry rotation apparatus 112 is provided that enables the rotation of the gantry 20 about its vertical axis (e.g.; axis of propagation 21a) to reduce the profile of the radiological imaging device 1 and thus, provide ease in transportation of the radiological imaging device 1. In one embodiment, both the horizontal gantry rotation apparatus 40 and the vertical gantry rotation apparatus 112 can be included with the radiological imaging device 1.

In another embodiment, the vertical gantry rotation apparatus 112 includes a first rotational base plate 113 or vertical axial rotation base plate (FIG. 2A), which is mounted to the gantry 20 (preferably, to the static ring 104 described above) and a second rotational base plate 114 or vertical rotation plate (FIG. 4A), which is mounted to the transportation mechanism 25 supporting the gantry 20. The first rotational base plate 113 rests above and is in parallel with the second rotational base plate 114. The first 113 and second 114 rotational base plates are separated by plurality of ball bearings 115 or vertical axis rotation ball bearings (FIG. 4A), that are integrated into the first 113 and second 114 rotational base plates. Each ball bearing 115 of the plurality of ball bearings 115 is covered by a ball bearing cover 116 or vertical rotation ball bearing cover (FIGS. 2A and 4B), provided in the first rotational base plate 113. In some embodiments, there are at least, three, and preferably four, ball bearings 115 to provide triangulation and separation of the first 113 and second 114 rotation base plates.

The ball bearings 115 of the vertical gantry rotation apparatus 112 allow the gantry 20 to rotate around its vertical axis 101 (FIG. 3A) via the first rotational base plate 113 with minimal resistance or friction and with increased stability. A vertical rotation cable is also attached to the gantry 20 and runs through a pathway 147 or vertical rotation cable pathway (FIG. 4B), provided in an area between the first 113 and second 114 rotational base plates and the ball bearings 115, such that the gantry 20 can be manually rotated about its vertical axis 101 or the axis of rotation, as shown in FIG. 3A. In this embodiment, it is assumed that the vertical axis 101 is substantially perpendicular to the axis of the bore 100 of the gantry 20 and intersects the first rotational base plate 113 or vertical axial rotation base plate (as in FIG. 2A).

In some embodiments, the rotation of the gantry 20 about its vertical axis 101 can be controlled via the control unit 30. After rotation of the gantry 20 around its vertical axis 101, the gantry 20 can be manually locked into a fixed position. In one embodiment herein, the vertical gantry rotation apparatus 112 rotates the gantry 20 up to ninety degrees (90°) about its vertical axis 101. Although the disclosed embodiment utilizes ball bearings 115 integrated into the first 113 and second 114 rotational base plates, the ball bearings 115 could also be placed into position via support collars, cut-outs or frames provided within the base plates, frameless systems, and/or other various mountings or restraints. The ball bearings 115 can also be provided in any number of shapes and sizes, and in any quantity that allows for the vertical rotation of the gantry 20. Alternatively, the ball bearings 115 could be removed entirely and the rotational base plates 113 and 114 could merely rotate via application of appropriate force with the presence of sufficient lubrication. In another embodiment, the vertical gantry rotation apparatus 112 includes a sensor (not shown) that signals the gantry 20 and/or the receiving device to disable movement along the axis of extension 20a, when the gantry 20 has been vertically rotated and is in a transport mode. During this transport mode, the receiving device can collect images, but the signal sent by the sensor prevents the linear scanning motion of the gantry 20 along the axis of extension 20a.

The specific components and configuration of the vertical gantry rotation apparatus 112 of the embodiment discussed above can be altered without departing from the spirit of the invention. In another embodiment, for example, the vertical gantry rotation apparatus 112 includes horizontal or vertical wheels on a guide track, a screw base, an electric rotational motor, lubricated planes, air-separated plates, magnetic levitation, or low-frictional plates. Alternatively, other solutions of creating large scanning diameters with high transportability include, for example, collapsible/retractable/telescoping gantries, gantries of fixed or variable sizes, modular gantry systems that are disassembled and reassembled for use, separable bed/gantry units, and variable shape gantries (i.e., C arms, etc.)

In one embodiment, the radiological imaging device 1 is provided with a lifter system 117, which enables the radiological imaging device 1 to scan a patient at varying elevations and/or angles of inclination. Accordingly, the lifter system 117 allows for decreased distances to scan targets, and alignment of the gantry bore axis 100 with target axes to increase image quality and accommodate variable target heights and volumes. In this embodiment, the lifter system 117 can be included with the radiological imaging device 1 in combination with the horizontal 40 and the vertical 112 gantry rotation apparatuses.

In one embodiment, the lifter system 117 includes a modular, two-piece device that slides underneath and connects to at least two sides of the transportation mechanism 25 supporting the gantry 20. In particular, the lifter system 117 includes at least one horizontally-oriented, piston-driven scissor system 118 or lifter system scissor (as in FIG. 5B), that connects to the wheel frame. Specifically, the piston-driven scissor system 118 connects to the v-shaped brackets 22 of the transportation mechanism 25 at lifter connection points 119 (as in FIG. 5A), via lifter connection pins 120 (as in FIG. 5B). In addition, the lifter system 117 includes a lifter piston crank 121 (as in FIG. 5A), that is either driven manually, hydraulically, or via an electric motor that is integrated into the lifter system 117 or attached externally. After positioning and connecting the lifter system 117 to one or both sides of the transportation mechanism 25, the lifter piston crank 121 of the lifter system 117 is driven in order to increase the vertical height of the piston-driven scissor system 118.

In some embodiments, the lifter piston crank 121 includes a gear system that pushes bracket members of piston-driven scissor system 118 bilaterally, as the gear system rotates, in order to cause the bracket members to lift or lower. As the vertical height of the piston-driven scissor system 118 increases, the side of the transportation mechanism 25 under which the lifter system 117 is positioned, is lifted. If a lifter system 117 is positioned underneath and connected to both sides of the transportation mechanism 25, both sides of the transportation mechanism 25 can be lifted simultaneously or independently. In addition, each side of the transportation mechanism 25 can be lifted to differing elevations depending on the imaging desired and/or each lifter system 117 can have differing height capabilities.

According to one embodiment, the lifter systems 117 can be controlled manually or by linking the lifter system 117 to the control unit 30 of the radiological imaging device 1, which allows for automation, control via software, device control stations, or a remote controller. In particular, in some embodiments, the user can select the appropriate gantry height and/or inclination on the control unit 30, and the lifter system 117 can orient itself accordingly, such that the user can then proceed with use and image scanning. In another embodiment, a shroud, such as a rubber cover, can be provided to encase each of the lifter systems 117, such that a patient does not interfere with components of the lifter system 117 during positioning of the patient and/or imaging. In addition, ball bearings 115 can be provided underneath lower braces of the lifter system 117 in order to allow for ease in transportation and positioning of the lifter system 117 underneath the transportation mechanism 25.

The specific components and configuration of the lifter system 117 of the embodiment discussed above can be altered without departing from the spirit of the invention. In another embodiment, for example, the lifter system 117 can be modified such that each wheel or wheel base of the transportation mechanism 25 can be lifted independently or simultaneously. In other example embodiments, for example, the lifter system 117 can be integrated into the transportation mechanism 25 and/or include gears, motors, hydraulic (e.g., air, fluid, etc.) pistons, air-inflated devices, magnetic levitators, or manual manipulation. Alternatively, other solutions of obtaining scans at varying angles include, for example, tilting the gantry 20 at its base, robotic arms to move the gantry 20 and/or the radiation source 21 and the at least one radiation detector 102, or a C arm of variable geometry.

In yet another embodiment, a roller support system 122 is provided with the radiological imaging device 1 that allows for a patient to be more easily placed into a desired position within the gantry 20, while avoiding interference with other components (e.g., table legs) of the radiological imaging device 1. In addition, the roller support system 122 provides support to the patient, patient bed, or bed extension, while also being configured to be raised and lowered to accommodate patient or table heights and/or variable target geometries. In one embodiment, the roller support system 122 is provided with at least one of the horizontal 40 and/or vertical 112 gantry rotation apparatuses, as well as with the lifter system 117.

In one embodiment, the roller support system 122 includes at least two vertical supports 123 or roller support vertical support (as in FIG. 5C), that are each positioned within a vertical collar 124 or roller support vertical collar, that are mounted within a housing of the gantry 20. The roller support system 122 further includes a horizontal roller support 50 or roller support horizontal, that includes a support roller 125 or roller support roller. The horizontal support roller 50 is reversibly mounted to the at least two vertical supports 123. The at least two vertical supports 123 can also be raised or lowered to varying heights using, for example, pistons or set pins.

In one embodiment, the raising and/or lowering of the at least two vertical supports 123 can be controlled via the control unit 30 of the radiological imaging device 1. In this embodiment, the user can select a desired height of the vertical supports 123 on the control unit 30, and the roller support system 122 raises or lowers accordingly. In addition, the raising and lowering of the vertical supports 123 and/or the roller support system 122 can be set by selecting values or iteratively pressing a button on the control unit 30 or another display panel provided with the radiological imaging device 1.

Figure 12A:
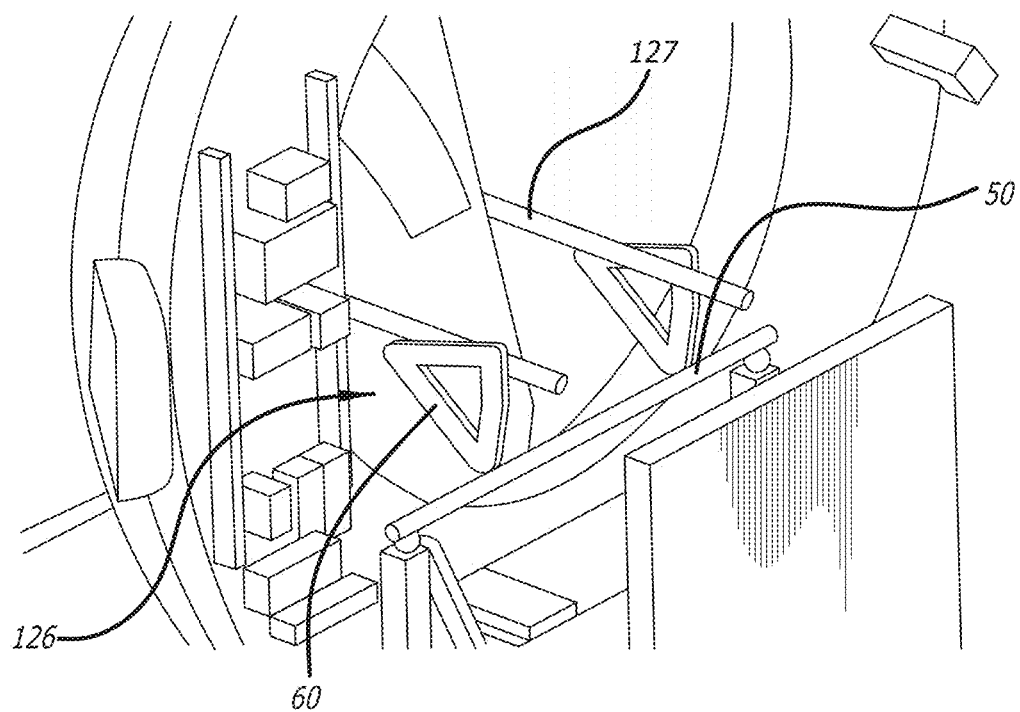
FIG. 12A illustrates a partial view of a configuration of the roller support system according to an example embodiment herein.
Figure 12B:
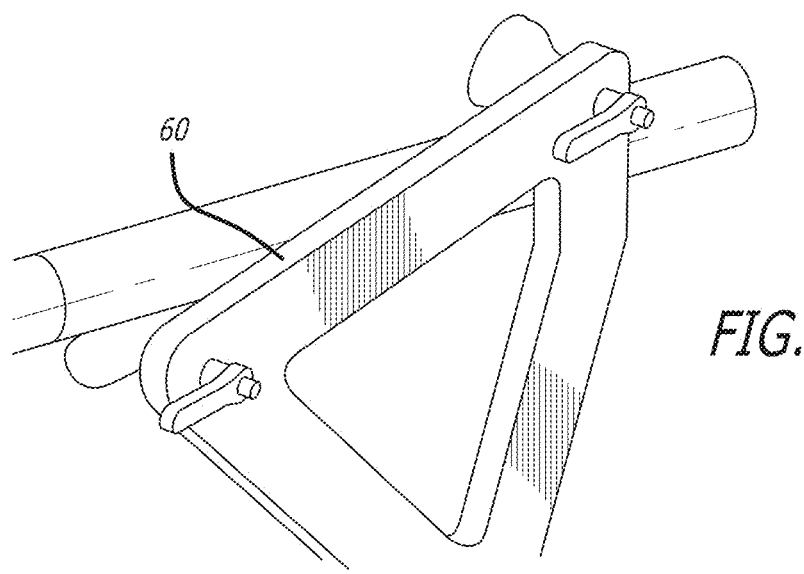
FIG. 12B illustrates a partial view of a configuration of the roller support system shown in FIG. 12A.

In another embodiment, the horizontal support roller 50 of the roller support system 122 slides into mounting holes provided within inner edges of the gantry bore 126 (not shown), such that the roller support system 122 can be integrated with the gantry 20. In some other embodiments, the roller support system 122 can include a fixed cantilever support 127 that includes at least two cantilever members 60 (as shown in FIGS. 12A and 12B) attached to the horizontal roller support 50 and, preferably, suitable to rotate with respect to the horizontal roller support 50 and the fixed cantilever support 127, in order to place the patient and/or the table, bed, or bed extension into the proper position. The horizontal support roller 50 of the roller support system 122 can be entirely removed from the gantry bore 126 and the vertical collars 124 in order to increase the size of the gantry bore 126. Although the disclosed embodiment uses a singular horizontal support roller 50, the horizontal support roller 50 could comprise multiple bars, smaller pivot points, multiple rollers, and/or a v-shaped bar or bars.

The specific components and configuration of the roller support system 122 of the embodiment discussed above can be altered without departing from the spirit of the invention. Alternatively, other solutions for supporting the patient, the patient bed, or the bed extension can be achieved by using, for example, lifting gears, motors, hydraulic (e.g., air, fluid, etc.) pistons, air-inflated devices, magnetic levitators, manual manipulation, plates with rollers, wheels, lubrication, magnetic separators, belts, treads, or gear systems. In addition, a modular support could be constructed that is mounted to the ceiling, gantry, or the transportation mechanism 25 (e.g.; cart), or a specialized, rolling or ceiling/floor-mounted independent bed could be employed in order to support a prone patient.

In one embodiment, a cooling system 128 is provided in order to cool components that generate heat within the gantry 20. The cooling system 128, preferably, disposed and rigidly joined to the gantry source/detector ring 103, enables the performance of multiple scans in rapid succession by the radiological imaging device 1 with minimal heat buildup. In some embodiments, the cooling system 128 can be provided with at least one of the horizontal 40 and/or vertical 112 gantry rotation apparatuses, as well as with the lifter system 117 and/or roller support system 122. In the example embodiment, the cooling system 128 includes a blow-through, fan-type cooling unit 129 (FIG. 2A) mounted to the gantry 20 and connected to either a backside or a front side of the radiation source 21 or X-ray source. In particular, the cooling system 128 includes a fluid-fed (preferably, glycol-fed) cooling unit 129 with a cooling unit fan 130 or cooling unit fan (as in FIG. 6A), and cooling unit fluid lines 131 or cooling unit glycol lines. The cooling system 128 blows cool air via the cooling unit fan 130 across the fluid lines 131 to transfer heat from the fluid lines 131 to the air.

Continuing with the current embodiment, the cooling unit 129 is mounted to the gantry 20 and connects to either the backside or the front side of the radiation source 21, such that "cold" fluid lines are fed from the cooling unit 129 into the radiation source 21 and run through an oil reservoir that surrounds radiation source 21 components to absorb heat from the oil via liquid-liquid heat exchange. The radiation source 21 further includes a pump, which can recirculate the oil in the oil reservoir to uniformly heat the oil and therefore, to enable a better liquid-liquid heat exchange. The "hot" fluid lines that absorb heat from the oil are then fed back into the cooling unit 129 in order to be cooled down using the cooling unit fan 130 and thus completing the cycle. The functions of the cooling system 128 can be, for example, continuous or controlled via the control unit 30. In particular, in one embodiment, the cooling system 128 is linked to the control unit 30 with a PC or PLC, which controls the radiation source 21 and the readings of the cooling system 128, such as, the temperature of the cooling unit 129 (by a temperature sensor disposed in the fluid lines and/or the oil reservoir), can be displayed on the interface of the PC, PLC, or the control unit of the source 21.

The specific components and configuration of the cooling system 128 of the embodiment discussed above can be altered without departing from the spirit of the invention. Alternatively, or in addition to the cooling system discussed above, a cooling system 128 can be provided on the backside of the radiation detector 102 in order to provide cooling to components placed on the radiation detector 102 side of the radiological imaging device 1. Cooling can also be achieved by using, for example, gas, water, or other refrigerants in a plate/frame exchanger, or any other type of heat exchanger known in the art.

In another embodiment, a source tilting device 132 is provided with the radiological imaging device 1 to position the radiation source 21 and thus, the central axis of propagation 21a of the radiation at various angles depending on the desired scanning position. Accordingly, the source tilting device 132 enables dynamic scanning that continually uses optimal offset distance and greater target volumes to be scanned by the gantry 20, which in turn increases the field-of-view (FOV) by increasing the angle of radiation emitted by the radiation source 21. The source tilting device 132 also optimizes beam targeting by keeping the strongest beam of radiation focused on the radiation detector 102.

In one embodiment, the source tilting device 132 is provided with at least one of the horizontal 40 and/or vertical 112 gantry rotation apparatuses, as well as with the lifter system 117, the roller support system 122, and/or the cooling system 128. In the embodiment herein, the source tilting device 132 includes an off-axis motor 133 or tilting source off-axis motor (as in FIG. 6B), that is connected to a piston system 134 or tilting source piston system, that is mounted to a source mounting plate 135 to which the radiation source 21 or X-ray source, is mounted. The source mounting plate 135 is mounted to the gantry 20 via a pivot support 136 or tilting source pivot support.

The source tilting device 132 allows for repositioning of the radiation source 21 and/or the angle of radiation emission by driving the off-axis motor 133 and thus, the piston system 134. In particular, as the off-axis motor 133 is driven, a drive axis of the off-axis motor 133 is rotated and this rotation is converted into either a linear extension or a linear retraction via the piston system 134. Since the piston system 134 is connected to the source mounting plate 135, the linear extension or retraction of the piston system 134 pushes against or pulls back the source mounting plate 135, which causes the source mounting plate 135 to freely rotate about the pivot point; thereby, shifting the angle of the radiation source 21 and/or the angle of radiation emission. The driving of the off-axis motor 133 to enable the source tilting device 133 to shift the angle of the radiation source 21 to a desired angle of radiation emission can be controlled via the control unit 30.

In one embodiment, the user selects the desired angle of the radiation source 21 on the control unit 30, and the source tilting device 132 orients the radiation source 21 accordingly, such that the user can then proceed with the image scanning. In some other embodiments, the source tilting device 132 is used in combination with the collimator 76 having an adjustable window, which provides the radiological imaging device 1 with great control over the FOV. In another embodiment, the radiation source 21 is tilted via the source tilting device 132 by varying degrees, to allow an optimized angle of radiation with respect to the scanning and target volume involved. For example, in one embodiment, the radiation source 21 is tilted from about 20 degrees to about 40 degrees. In another embodiment, the source is tilted via the source tilting device 132 from about −17.5 degrees to about +17.5 degrees from its "rest" position, thus providing for a total angle sweep of about 35 degrees.

The specific components and configuration of the source tilting device 132 of the embodiment discussed above can be altered without departing from the spirit of the invention. In another embodiment, for example, the source tilting device 134 includes gears, direct drive rotational motors (at the pivot point), belts, manual manipulation, chains, scissor systems, solenoids, low-slip nearing systems, or robotic arm mounts. Alternatively, other solutions of dynamic scanning to continually use optimal offset distance and increasing the FOV can include, for example, tilting the radiation detector 102 (with or without tilting the radiation source 21), increasing the radiation detector 102 size (thereby, increasing the radiation dose), increasing the radiation detector 102 and/or the radiation source 21 quantity, increasing the emission angle of the radiation source 21, translating the radiation source 21, or decreasing the distance between the radiation source 21 and the radiation detector 102.

In yet another embodiment, a translational apparatus 137 is provided that is adapted (i) to displace the radiation detector 102 with respect to the radiation source 21, and (ii) to displace the radiation detector 102 horizontally with respect to inner edges of the gantry 20 (e.g.; side-to-side). Accordingly, the translational apparatus 137 allows for obtaining scans of at least a portion of the patient with improved image quality, increases clearance of the gantry bore 126 for scanning procedures, provides for dynamic scanning that continually uses optimal offset distance, and increases scanning diameter capabilities.

In one embodiment, the translational apparatus 137 is provided with at least one of the horizontal 40 and/or vertical 112 gantry rotation apparatuses, as well as with the lifter system 117, the roller support system 122, the cooling system 128, and/or the source tilting device 132. The translational apparatus 137 includes a translational plate 138 or the Detector Mounting Plate (as in FIG. 6C) to which the radiation detector 102 or Detector (as in FIG. 6C) is mounted, a first linear actuator 139, and a second linear actuator 140. The first linear actuator 139 moves the radiation detector 102 along a first direction of translation, which is substantially perpendicular to the central axis of propagation 21a and, preferably, substantially perpendicular to the axis of extension 20a. Similarly, the second linear actuator 140 moves the radiation detector 102 along a second direction of translation, which is substantially parallel to the central axis of propagation 21a.

The first linear actuator 139 includes a first motor 141 or horizontal translation plate motor (as in FIG. 6C), a horizontal plate support 142 or horizontal translation plate support, and a horizontal chain 143 or horizontal translation plate chain. Similarly, the second linear actuator 140 includes a second motor 144 or vertical translation plate motor, a vertical plate support 145 or vertical translation plate support, and a vertical chain 146 or vertical translation plate chain. The first motor 141 drives the horizontal chain 143 and/or the horizontal plate support 142, such that the translational plate 138 and the radiation detector 102 is horizontally driven (e.g.; side-to-side) along the horizontal plate support 142. The second motor 144 drives the vertical chain 146 and/or the vertical plate support 145, such that the translational plate 138 and the radiation detector 102 is vertically driven (e.g.; toward or away from the central bore axis of the gantry 100) along the vertical plate support 145.

In some embodiments, the first 141 and the second 144 motors are controlled by automation software installed in the control unit 30 and/or other device interfaces. In such cases, once the user selects a desired position of the radiation detector 102 on the control unit 30, the translational apparatus 137 orients the radiation detector 102 according to the user's instruction, to enable the user to proceed with the image scanning in desired setting. In one embodiment, by horizontally translating and/or vertically retracting the translational plate 138 and the radiation detector 102, images are captured at greater angles with greater FOVs, with or without tilting the radiation source 21. Moreover, in some embodiments, the translational apparatus 137 is included with the source tilting device 132 to achieve even greater FOVs.

The specific components and configuration of the translational apparatus 137 of the embodiment discussed above can be altered without departing from the spirit of the invention. In yet another embodiment, the translational apparatus 137 includes gears, belts, manual manipulation, chains, scissor systems, solenoids, magnetic levitators, low-slip bearing systems, hydraulic lifters, pistons, or robotic arm mounts. Alternatively, in case a user performs a dynamic scanning using optimal offset distance, image quality can be improved by decreasing the distance between the radiation source 21 and the target. This can be achieved by mounting the radiation source 102 to an analogous translational apparatus 137, or by using a smaller gantry 20, robotic armature, or C-arm mounting with pivot points.

Figure 7A:
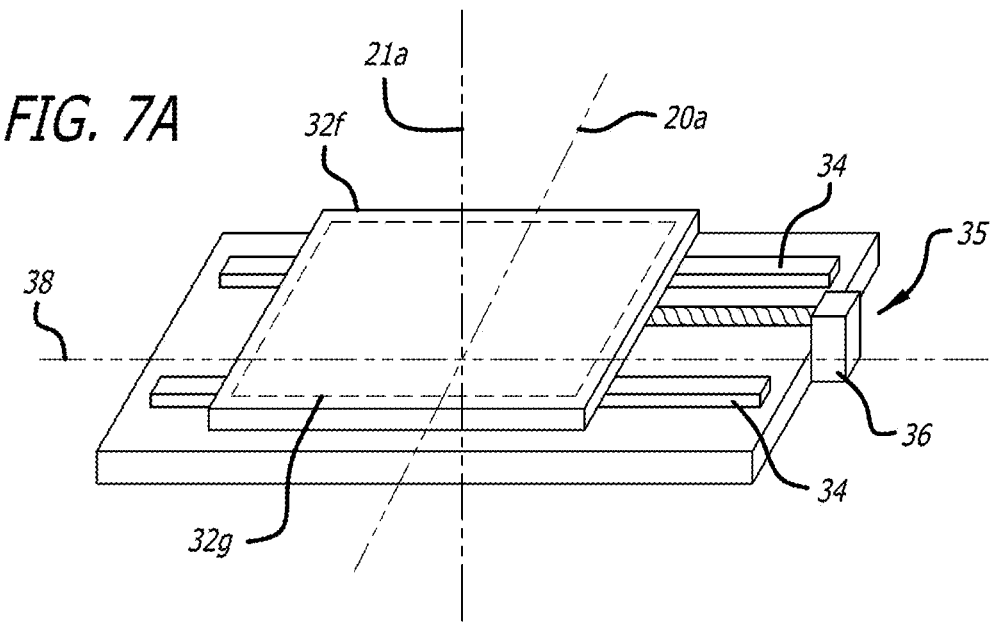
FIG. 7A illustrates a matrix mode of a flat panel sensor subassembly of the imaging device of FIG. 1 according to an example embodiment herein.
Figure 7B:
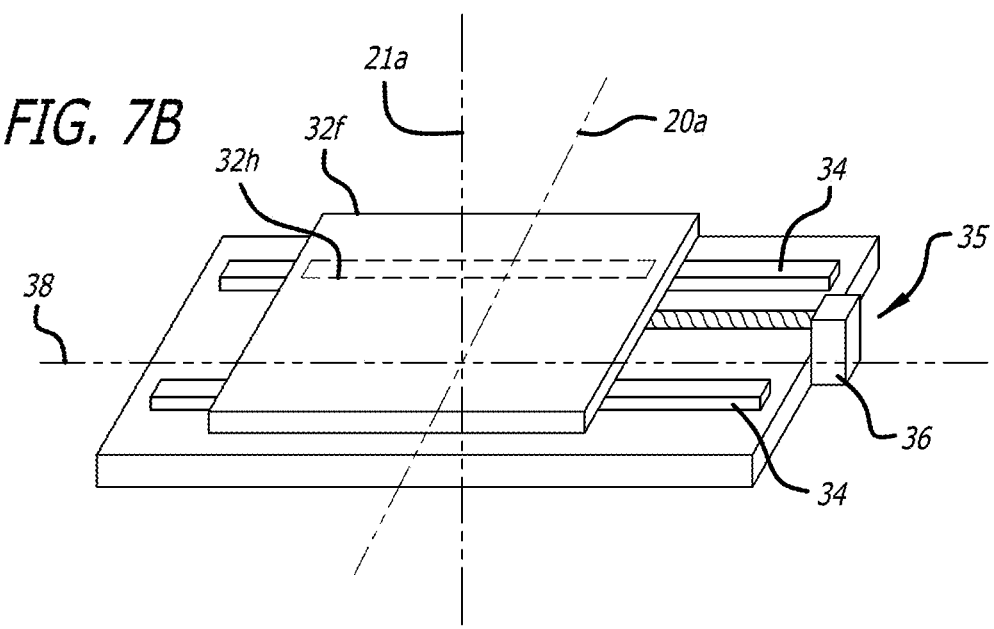
FIG. 7B illustrates a linear sensor mode of a flat panel sensor subassembly of the imaging device of FIG. 1 according to an example embodiment herein.

Following is an embodiment of the radiation detector 102. In this embodiment, the radiation detector 102 includes at least one flat panel sensor 32*f* (as shown in FIGS. 7A and 7B), that includes an array of pixels. The flat panel sensor 32*f* is capable of operating in multiple independent read-out modes, including a matrix mode (FIG. 7A) and a linear sensor mode (FIG. 7B). The independent read-out modes of the flat panel sensor 32*f* are selectable by control unit 30. In this embodiment, operating the flat panel sensor 32*f* in the matrix mode is referred to as the first active configuration, and operating the flat panel sensor 32*f* in the linear sensor mode is referred to as the second active configuration of the radiation detector 102, respectively.

In the first active configuration (i.e.; the matrix mode; FIG. 7A), the flat panel sensor 32*f* outputs signal corresponding to the radiation detected by the pixels in a region of sensitive surface 32*g* of the flat panel sensor 32*f* (FIG. 7A) to the control unit 30. In one embodiment herein, the sensitive surface 32*g* is substantially coextensive with the entire array of pixels of the flat panel sensor 32*f*. The matrix mode of the flat panel sensor is suitable for performing at least tomography and fluoroscopy.

In the second active configuration (i.e.; linear sensor mode; FIG. 7B), the flat panel sensor 32*f* outputs signals corresponding to the radiation detected by the subset of pixels in a region of sensitive surface 32*h* of the flat panel sensor 32*f* (FIG. 7A), to the control unit 30. The sensitive surface 32*h* of the flat panel sensor 32*f* functions effectively as a linear sensor. Specifically, in this embodiment, the sensitive surface 32*h* has a frame rate in the range of approximately 10-300 frames per second and a width that is substantially greater than its length. In this case, the length of the sensitive surface 32*h* is defined in a direction substantially parallel to the axis of extension 20*a*, wherein the width of the sensitive surface 32*h* is defined in a direction substantially perpendicular to the axis of extension 20*a* and the central axis of propagation 21*a*.

The second active configuration of the flat panel sensor 32*f* is useful for performing fan beam tomography. As described with reference to FIG. 2C, fan beam tomography can be performed by shaping the radiation emitted by the radiation source 21 into a fan-shaped beam using, for example, a collimator 76. However, by selecting a portion (i.e., a subset) of the flat panel sensor 32*f* as a radiation sensitive surface, the flat panel sensor 32*f* can operate in multiple modes. Moreover, switching from fan beam imaging to cone beam imaging can be easily achieved by selecting a subset of the flat panel sensor 32*f* as a radiation sensitive surface, without altering the operation of radiation source 21 or physically interchanging any components of the radiological imaging device 1. That is, for a cone-shaped beam of radiation, operating the flat panel sensor 32*f* in the linear sensor mode will provide the sensitive surface 32*h* that is effectively sensitive only to a fan-shaped cross-section of the cone-shaped beam of radiation. Accordingly, when the radiation source 21 emits a cone-shaped beam of radiation, cone beam tomography can be performed using the control unit 30. For example, the matrix mode of flat panel sensor 32*f* and fan beam tomography can be performed by selecting via control unit 30, for example, the linear sensor mode of flat panel sensor 32*f*.

The pixel array size of sensitive surfaces 32*g* and 32*h* of the flat panel sensor 32*f* can be predefined in hardware, firmware, software, or other control means of the flat panel sensor 32*f*. In one embodiment, the flat panel sensor 32*f* may be a Hamamatsu model C11701DK-40 flat panel sensor, which can operate in a matrix mode that provides a sensitive surface 32*g* having a 1096×888 or a 2192×1776 array of pixels. Moreover, the Hamamatsu model C11701DK-40 flat panel sensor can also separately operate in a linear sensor mode that provides a sensitive surface 32*h*, having a 1816× 60 array of pixels.

In some embodiments, the flat panel sensor 32*f* can be mounted on a panel motion system 35 that includes guides 34 and a motorized transportation mechanism 36 (FIGS. 7A and 7B). The panel motion system 35 is suitable for moving the flat panel sensor 32*f* along an axis 38, which is substantially perpendicular to both the axis of extension 20*a* and the central axis of propagation 21*a*. In one embodiment, during the linear mode of operation of the flat panel sensor 32*f*, the axis 38 remains parallel to the width of the sensitive surface 32*h* of the flat panel sensor 32*f*.

Figure 10:
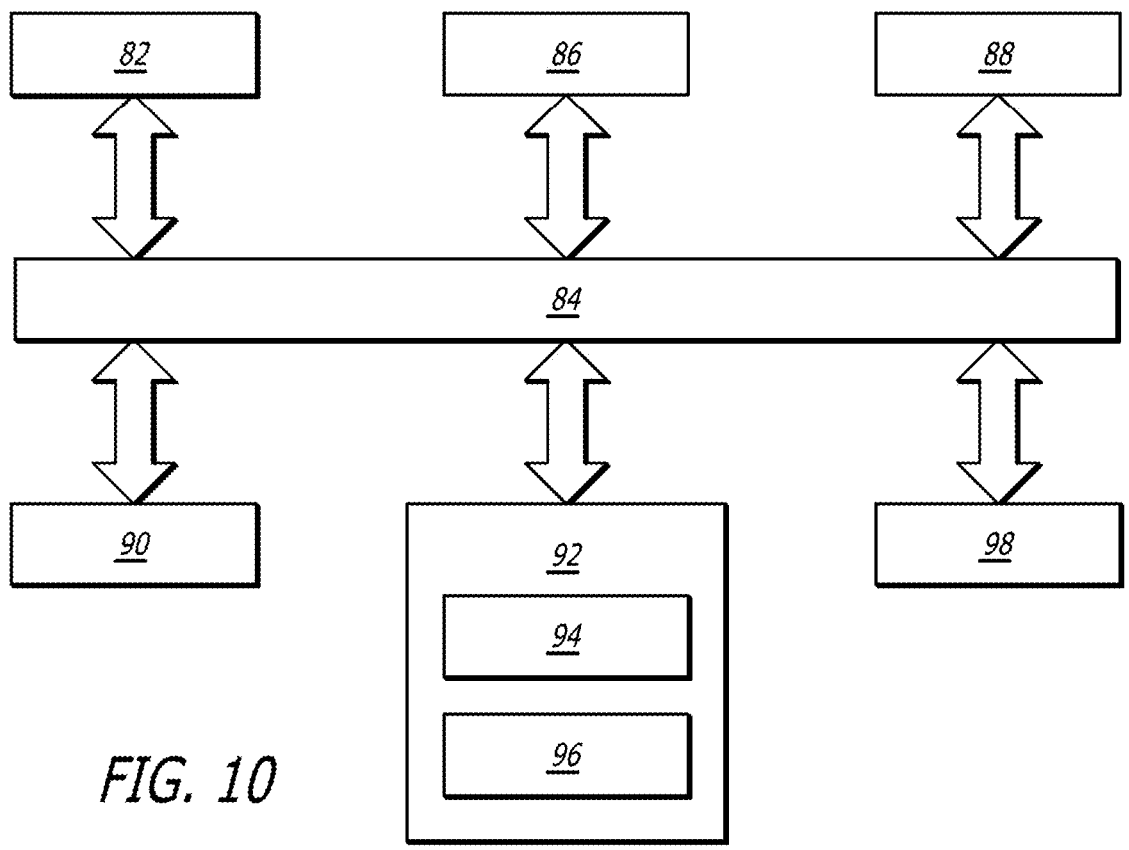
FIG. 10 illustrates a block diagram of an example computer system of the radiological imaging device shown in FIG. 1.

According to an embodiment, FIG. 10 illustrates a schematic block diagram representation of a computer system 80. In this embodiment, it is assumed that at least some components of the computer system 80 can form or be included in the aforementioned control unit 30. The computer system 80 is electrically connected to other components of the radiological imaging device 1 (e.g.; the radiation source 21, the radiation detector 102, the gantry 20, and any subcomponents thereof) by way of communications interface 98. The computer system 80 includes at least one computer processor 82 ("controller") including a central processing unit, a multiple processing unit, an application-specific integrated circuit ("ASIC"), a field programmable gate array ("FPGA"), or the like. The processor 82 is connected to communication infrastructure 84 (e.g., a communications bus, a cross-over bar device, or a network). Although various embodiments are described herein in terms of this exemplary computer system 80, after reading this description, it will become apparent to a person skilled in the relevant art(s) how to implement the invention using other computer systems and/or architectures, and doing so is within the scope of the invention.

In some other embodiments, the computer system 80 may also include a display unit 86 for displaying video graphics, text, and other data provided from the communication infrastructure 84. The display unit 86 can be included in the control unit 30. In yet another embodiment, the computer system 80 further includes an input unit 88 that can be used by the operator to send information to the computer processor 82. For example, the input unit 88 can include a keyboard device and/or a mouse device or other input device(s). In some cases, the display unit 86, the input unit 88, and the computer processor 82 can collectively form a user interface. In case of a computer system 80 enabled with a touch screen display, the input unit 88 and the display units 86 are combined. In such cases, if an operator touches the display unit 86, the display unit converts the touch signal into a corresponding electrical signal and sends that signal to the processor 82.

In addition, the computer system 80 includes a main memory 90 (e.g.; a random access memory ("RAM") and a secondary memory 92. The secondary memory 92 includes a hard disk drive 94 and/or a removable storage drive 96 (e.g., a floppy disk drive, a magnetic tape drive, an optical disk drive, a flash memory drive, and the like) capable of reading from and writing to a corresponding removable storage medium, in a known manner. The removable storage medium can be a non-transitory computer-readable storage medium storing computer-executable software instructions and/or data.

In yet another embodiment, the computer system 80 include a communications interface 98 (e.g.; a modem, a network interface (e.g.; an Ethernet card), a communications port (e.g., a Universal Serial Bus ("USB") port or a FireWire® port), and the like) that enables software and data to be transferred between the computer system 80 and external devices. For example, the communications interface 98 can be used to transfer software or data between the computer system 80 and a remote server or cloud-based storage (not shown). Additionally, the communication interface 98 can be used to transfer data and commands between the computer system 80 (serving as control unit 30) to other components of the radiological imaging device 1 (e.g.; the radiation source 21, the radiation detector 102, the gantry 20, and any subcomponents thereof).

One or more computer programs (also referred to as computer control logic) are stored in the main memory 90 and/or the secondary memory 92 (e.g.; the removable-storage drive 96 and/or the hard disk drive 94). The computer programs can also be loaded into the computer system 80 via the communications interface 98. The computer programs include computer-executable instructions which, when executed by the controller/computer processor 82, cause the computer system 80 to perform the procedures described herein and shown in FIG. 8. Accordingly, the computer programs can control the control unit 30 and other components (e.g., the radiation source 21, the radiation detector 102, the gantry 20, and any subcomponents thereof) of the radiological imaging device 1.

Figure 8:
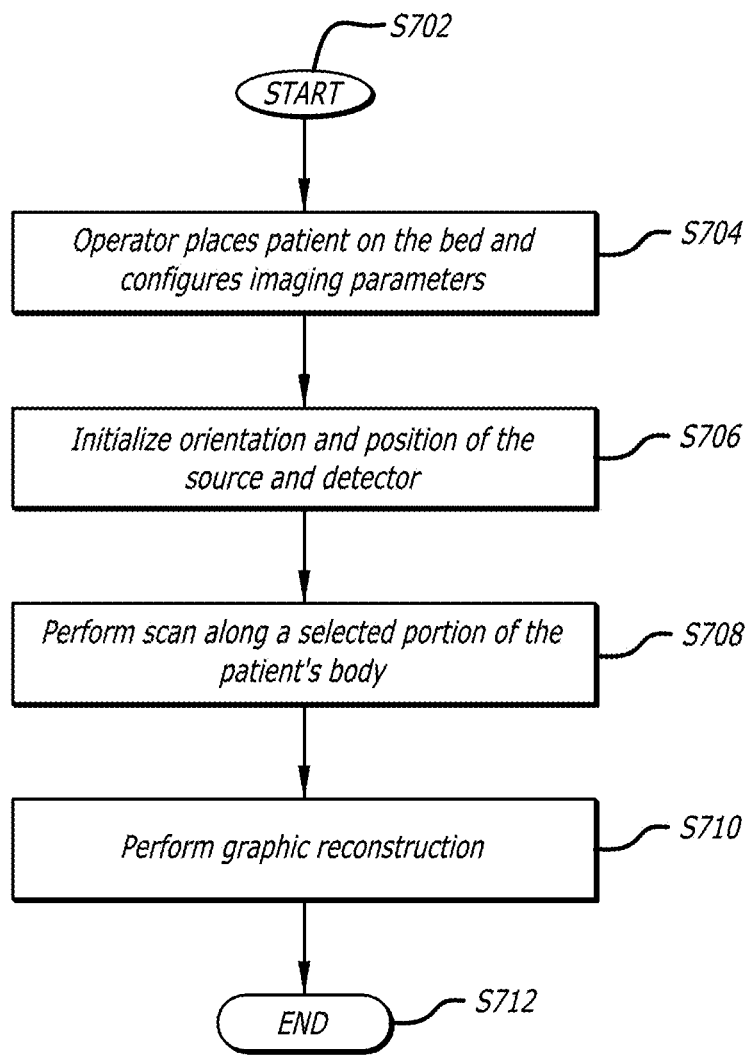
FIG. 8 is a flowchart illustrating an imaging procedure according to an example embodiment herein.

A process of scanning at least a portion of a patient using the radiological imaging device 1 will now be further described with reference to FIG. 8. At S702 the radiological imaging device 1 initializes itself to perform the scanning process. Next, at S704, the operator places the patient on a bed. In some embodiments, the operator then activates the laser positioning system (including lasers 72 and 74, as shown in FIGS. 9A and 9B), which projects horizontal visual markers 73 to assist the operator in adjusting the height and inclination of the patient in reference to the gantry 20. The laser positioning system also projects a top-down marker 75 to assist the operator in laterally adjusting the patient in reference to the gantry 20. Accordingly, the operator adjusts the position of the patient and/or the bed or bed extension within the gantry 20 using the roller support system 122.

Additionally, at S704, the operator may operate the control unit 30 to specify imaging parameters, such as, the portion of the body on which to perform a total body scan and the inclination of the central axis of propagation with or without shifting the radiation source 21 using the source tilting device 132. In some embodiments, the operator also inputs patient information (e.g., species, weight, and/or tissue type to be imaged) in the control unit 30 and commands the control unit 30 to automatically configure the radiological imaging device 1 to select the appropriate radiation dose based on the patient information.

Next, at S706, the control unit 30 responds to the aforementioned operator specified imaging parameters and controls the horizontal gantry rotation apparatus, so as to rotate the source 21 and the detector in order to orient the central axis of propagation 21a in relation to the patient and/or bed. In addition, the control unit 30 can control the position of the radiation source 21 via the source tilting device 132, the position of the transportation mechanism 25 and/or gantry 20 via the lifter system 117, and/or the position of the radiation detector 102 via the translational apparatus 137, according to the user specific parameters. Moreover, if the operator commands the control unit 30 to automatically configure the radiological imaging device 1 to use an appropriate radiation dose in S704, the control unit 30 configures the source 21 and the filter 76, if necessary, in the manner described above, so as to be prepared to provide such a dose. Once the central axis of propagation 21a has reached the desired inclination, the radiological imaging device 1 starts scanning at S708.

At S708, during scanning of the patient's body, the horizontal gantry rotation apparatus 40 rotates the gantry source/detector ring 103 so that the radiation source 21 and the radiation detector 102 rotate together, thereby permitting the radiation to scan the entire analysis zone 20b to be imaged. As the rotation of the gantry source/detector ring 103 continues, the radiation source 21 emits radiation. Such radiation, after traversing the patient's body, is detected by the radiation detector 102, which in turn sends a corresponding electrical signal to the control unit 30.

The manner in which S708 is performed in a case where the radiation detector 102 includes a flat panel sensor 32f operating in a linear sensor mode with sensitive surface 32h will now be described. During a scan, the radiation source 21 continuously emits radiation, which traverses the patient's body and hits the sensitive surface 32h of the flat panel sensor 32f. As the gantry source/detector ring 103 rotates, the flat panel sensor 32f detects radiation during such rotation and sends corresponding electrical signals to the control unit 30. Accordingly, the control unit 30 receives a signal for the entire zone imaged and processes the signal to acquire an image of the scanned part of the patient.

In one embodiment, if desired by the operator, one or more additional scans may be performed. For each additional scan, the flat panel sensor 32f can be translated along axis 38 by the panel motion system 35 to a new position that partially overlaps the position of the flat panel sensor 32f in a previous scan, and more particularly, the immediately preceding scan. However, in some embodiments, for each additional scan, the radiation detector 102 is translated by using the translational apparatus 137. Next, a further scanning procedure is performed in the manner described above, that is, the gantry source/detector ring 103 is rotated while the radiation source 21 emits radiation and the flat panel sensor 32*f* continuously outputs a signal to the control unit 30. In this manner, a plurality of scans can be acquired, each scan being as wide as the sensitive surface 32*h*. The plurality of scans is then provided to the control unit 30 for graphic reconstruction at S710.

At S710, the control unit 30 carries out the graphic reconstruction of the zone being imaged using the readings performed by the radiation detector 103. In the example embodiment where the radiation detector 103 includes flat panel sensor 32*f* operating in the linear sensor mode, the plurality of scans acquired in S708 by flat panel sensor 32*f* can be reconstructed into one overall image in a manner that minimizes edge effects in overlapping regions of the plurality of images. Thus, by virtue of the panel motion system 35 and/or the translational apparatus 137, the flat panel sensor 32*f* can provide an overall radiological image that is wider than the sensitive surface 32*h*.

The process then continues to S712 and ends. The operator may repeat the process or a portion thereof to acquire additional scans, as desired.

In view of the foregoing description, it can be appreciated that at least some example embodiments described herein provide a radiological imaging device 1 that produces high quality total body scan images, and that can be used to perform computerized tomography, fluoroscopy and radiography in a single device.

Additionally, the radiological imaging device 1 can perform dynamic scanning to continually use optimal offset distance, increased FOV imaging, different analyses, and/or various angled imaging on the patient without having to move said patient, and, as a consequence, risks associated with such maneuvers may be reduced or substantially minimized.

In addition, since it is possible to select the most suitable detector at the most suitable position of the radiation detector 102, the radiation source 21, and/or the gantry 20 for each analysis, the radiological imaging device 1 makes it possible to limit, or substantially reduce or minimize, exposure to X-rays.

An innovative radiological imaging procedure also is provided by virtue of the radiological imaging device 1. With the radiological imaging procedure, the analysis can be performed when the patient and the device is in the ideal condition, thus limiting exposure to radiation and the costs of the analysis.

Additionally, by virtue of the radiological imaging device 1, it is possible to perform total body scanning at 360° and without moving the patient during the entire procedure.

In further example embodiments, the at least one horizontal gantry rotation apparatus, vertical gantry rotation apparatus, lifter system, rolling support system, cooling system, source tilting device, and translational apparatus, discussed above, could also be included with the radiological imaging devices according to one or more of the example embodiments described in U.S. Provisional Patent Applications Nos. 61/932,024, 61/932,028, 61/932,034, and 61/944,956, which are incorporated herein by reference in their entireties, as if set forth fully herein.

While numerous preferred embodiments have been described herein, it is within the scope of the invention for a radiological imaging device to include one or a combination of any of the features described above.

Modifications and variations may be made to the example embodiments described herein without departing from the scope of the inventive concept. All the elements as described and claimed herein may be replaced with equivalent elements and the scope of the example embodiments includes all other details, materials, shapes and dimensions.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed:

1. A radiological imaging device comprising:
    a gantry defining an analysis zone in which at least a part of a patient is placed;
    a roller support system that mounts to the gantry, the roller support system including at least two vertical supports and at least one horizontal support mounted to the at least two vertical supports and comprising a fixed, cantilever support that includes at least two cantilever members that can be rotated to place the patient in a proper analysis position;
    a source arranged to emit radiation that passes through the at least part of the patient, the radiation defining a central axis of propagation;
    a detector arranged to receive the radiation when performing at least one of tomography, fluoroscopy, radiography, and multimodality and to generate data signals based on the radiation received; and
    a fluid-fed cooling system adapted to provide cooling for components that generate heat within the gantry.

2. The radiological imaging device of claim 1, further comprising:
    a horizontal gantry rotation apparatus that includes a ring to which the source and the detector are mounted and a rotational bearing member configured to rotate the ring; and
    a control unit adapted to acquire an image from data signals received continuously from the detector while the horizontal gantry rotation apparatus continuously rotates the ring and the source emitting the radiation and the detector receiving the radiation that are mounted to the ring, so as to scan the at least part of the patient.

3. The radiological imaging device of claim 1, wherein the cooling system includes a blow-through, fan-type cooling unit mounted to the source.

4. The radiological imaging device of claim 1, wherein the at least one horizontal support comprises at least one support roller.

5. The radiological imaging device of claim 1, further comprising a source tilting device that connects to the source, the source tilting device including:
    a source mounting plate to which the source is mounted;
    a source pivot support to which both the gantry and the source mounting plate are connected;

a piston system adapted to engage with the source mounting plate; and a motor that drives the piston system.

6. The radiological imaging device of claim 1, further comprising a translational apparatus configured to translate the detector, the translational apparatus comprising:

a translational plate to which the detector is mounted;

a first linear actuator configured to move the detector in a first direction of translation; and a second linear actuator configured to move the detector in a second direction of translation that is perpendicular to the first direction of translation.

7. A method of acquiring a radiological image of at least a part of a patient placed in a gantry, the method comprising:

causing a source in the gantry to emit radiation that passes through the at least part of the patient, the radiation defining a central axis of propagation;

mounting a roller support system to the gantry, the roller support system including at least two vertical supports and at least one horizontal support mounted to the at least two vertical supports and comprising a fixed, cantilever support that includes at least two cantilever members that can be rotated to place the patient in a proper analysis position;

receiving the radiation at a detector in the gantry when performing at least one of tomography, fluoroscopy, radiography, and multimodality;

cooling components that generate heat within the gantry using a fluid-fed cooling system; and outputting data signals from the detector to a control unit based on the radiation received.

8. The method of claim 7, further comprising:

continuously rotating the source and the detector with a horizontal gantry rotation apparatus around a bore axis of the gantry; and acquiring, at the control unit, an image from data signals received continuously from the detector while the horizontal gantry rotation apparatus continuously rotates the source emitting the radiation and the detector receiving the radiation, so as to scan the at least part of the patient.

9. The method of claim 7, wherein the cooling system includes a blow-through, fan-type cooling unit mounted to the source.

10. The method of claim 7, further comprising tilting the source using a source tilting device that connects to the source, the source tilting device including:

a source mounting plate to which the source is mounted; a source pivot support to which both the gantry and the source mounting plate are connected;

a piston system adapted to engage with the source mounting plate; and a motor that drives the piston system.

11. The method of claim 7, further comprising translating a position of the detector in relation to the patient with a translational apparatus, the translational apparatus comprising:

a translational plate to which the detector is mounted;

a first linear actuator configured to move the detector in a first direction of translation; and a second linear actuator configured to move the detector in a second direction of translation that is perpendicular to the first direction of translation.

12. The method of claim 7, wherein the at least one horizontal support comprises at least one support roller.

* * * * *